(12) United States Patent
Nudler et al.

US008889634B2

(10) Patent No.: US 8,889,634 B2
(45) Date of Patent: Nov. 18, 2014

(54) SHORT PEPTIDES USEFUL FOR TREATMENT OF ISCHEMIA/REPERFUSION INJURY AND OTHER TISSUE DAMAGE CONDITIONS ASSOCIATED WITH NITRIC OXIDE AND ITS REACTIVE SPECIES

(71) Applicant: New York University, New York, NY (US)

(72) Inventors: Evgeny A. Nudler, New York, NY (US); Ruslan R. Rafikov, Evans, GA (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/755,093

(22) Filed: Jan. 31, 2013

(65) Prior Publication Data
US 2013/0150283 A1 Jun. 13, 2013

Related U.S. Application Data

(62) Division of application No. 11/744,104, filed on May 3, 2007, now Pat. No. 8,389,482.

(60) Provisional application No. 60/887,314, filed on Jan. 30, 2007.

(51) Int. Cl.
*A61K 38/07* (2006.01)
*C07K 5/103* (2006.01)
*C07K 5/12* (2006.01)
*C07K 7/06* (2006.01)
*A61K 38/00* (2006.01)

(52) U.S. Cl.
CPC .............. *C07K 5/126* (2013.01); *C07K 5/1013* (2013.01); *A61K 38/00* (2013.01); *C07K 7/06* (2013.01)
USPC ...................................... 514/21.9

(58) Field of Classification Search
None
See application file for complete search history.

(56) References Cited

U.S. PATENT DOCUMENTS

| | | |
|---|---|---|
| 6,372,727 B1 | 4/2002 | Crow et al. |
| 2004/0072162 A1 | 4/2004 | Fomsagaard et al. |
| 2005/0084547 A1 | 4/2005 | Subbiah |
| 2005/0137196 A1 | 6/2005 | Timmer et al. |
| 2005/0214859 A1 | 9/2005 | Dransfield et al. |
| 2005/0250702 A1 | 11/2005 | Antonius Maria Strous et al. |
| 2006/0183913 A1 | 8/2006 | Assaf et al. |
| 2007/0015711 A1 | 1/2007 | Szeto |

FOREIGN PATENT DOCUMENTS

| | | |
|---|---|---|
| JP | 2005-170849 | 6/2005 |
| WO | WO2005/000338 | 1/2005 |
| WO | WO2005/049072 | 6/2005 |
| WO | WO 2008042421 | * 4/2008 |

OTHER PUBLICATIONS

Olshansky et al ('No truth to the fountain of youth' Scientific American Monday Dec. 29 2008, retrieved from http://www.scientificamerican.com/article.cfm?id=no-truth-to-the-fountain-of-youth&pri on Dec. 16, 2013, 4 pages).*
Hukkanen et al ('Aseptic loosening of total hip replacement' The journal of bone and joint surgery May 1997 v79-b pp. 467-474).*
Shemesh et al ('Thrombolysis for early failure of prosthetic arteriovenous access' Journal of Vacular Surgery Mar. 2008 pp. 585-590 with 1 appendix page).*
Portillo et al ('Prosthesis failure within 2 years of implantation is highly predictive of intection' Clin Orthop Relat Res (2013) v471 pp. 3672-3678).*
Aulak, et al., Dynamics of protein nitration in cells and mitochondria, AM J Physiol Heart Circ Physiol, vol. 286, pp. H30-H38, 2004.
Bian, et al., Proteomic Modification by Nitric Oxide, J. Pharmacol Sci., vol. 101, pp. 271-279, 2006.
Cauwels et al., Anaphylactic Shock Depends on PI3K and eNOS-Derived NO, Journal of Clinical Investigation, vol. 116, pp. 2244-2251, 2006.
Communication (European Office Action) regarding EP Application No. 07797333.7, dated Jan. 10, 2012.
Deneke, Thiol-Based Antioxidants, Current Topics in Cellular Regulation, vol. 36, pp. 151-180, 2000.
Egleton, et al., Development of Neuropeptide Drugs that Cross the Blood-Brain Barrier, The American Society for Experimental NeuroTherapeutics, vol. 2, pp. 44-53, 2005.
Glantzounis, et al., The Role of Thiols in Liver Ischemia-Reperfusion Injury, Current Pharmaceutical Design, vol. 12, pp. 2891-2901, 2006.
Gusarov, et al., NO-Mediated Cytoprotection: Instant adaptation to oxidative stress in bacteria, Proc. Natl. Acad. Sci. USA, vol. 102, pp. 13855-13860, 2005.
Ischiropoulos, Biological Tyrosine Nitration: A Pathophysiological Function of Nitric Oxide and Reactive Oxygen Species, Archives of Biochemistry and Biophysics, vol. 356, No. 1, pp. 1-11, 1998.
Kamisaki, et al., An activity in rat tissues that modifies nitrotyrosine-contalning proteins, Proc. Natl. Acad. Sci. USA vol. 95, Issue 20, pp. 11584-11589, 1998.
Nedospasov, et al., An Autocatalytic Mechanism of Protein Nitrosylation, Proc. Natl. Acad. Sci. USA, vol. 97, No. 25, pp. 13543-13548, 2000.

(Continued)

*Primary Examiner* — James H Alstrum Acevedo
*Assistant Examiner* — Ronald Niebauer
(74) *Attorney, Agent, or Firm* — Troutman Sanders LLP

(57) ABSTRACT

This invention discloses isolated short peptides comprising the amino acid sequence Cys-Glu-Phe-His (CEFH; SEQ ID NOS: 1 and 15) and analogs thereof as well as compositions comprising CEFH peptides and analogs thereof. The CEFH peptides disclosed herein are effective in mediating the denitration of 3-nitrotyrosines (3-NT) in cellular proteins thereby preventing tissue damage associated with excess nitric oxide (NO) and its reactive species. The CEFH peptides disclosed herein are useful in the treatment of ischemia/reperfusion (I/R) injury and other disorders.

8 Claims, 4 Drawing Sheets

(56) References Cited

OTHER PUBLICATIONS

Radi, Nitric Oxide, Oxidants, and Protein Tyrosine Nitration, Proc. Natl. Acad. Sci. USA, vol. 101, No. 12, pp. 4003-4008, 2004.

Rafikova, et al., Catalysis of S-Nitrosothiols Formation by Serum Albumin: The mechanism and implication in vascular control, Proc. Natl. Acad. Sci. USA, vol. 99, No. 9, pp. 5913-5918, 2007.

Rafikova, et al., Control of Plasma Nitric Oxide Bioactivity by Perfluorocarbons, Physiological Mechanisms and Clinical Implications, Circulation, vol. 110, pp. 3573-3580, 2004.

Rafikova, et al., Nitric Oxide Regulation of Cell Death, Cardiomyocyte fate in ischemia/reperfusion is controlled by nitric oxide, Nitric Oxide, vol. 14, A67-A68, 2006.

Schmidt, et al. Specific Nitration at Tyrosine 430 Revealed by High Resolution Mass Spectrometry as Basis for1 Redox Regulation of Bovine Prostacyclin Synthase, J. Biological Chemistry, vol. 278, No. 15, pp. 12813-12819, 2003.

Stamler, et al., Nitrosylation: The Prototypic Redox-based Signaling Mechanism, Cell, vol. 106, pp. 675-683, 2001.

Supplemental European Search Report for EP Application No. 07797333.7, dated Oct. 7, 2010.

Torchilin et al., Peptide and Protein Drug Delivery to an into Tumors: Challenges and Solutions, DDT, vol. 8, No. 6, pp. 259-266, 2003.

Turko et al., Protein Nitration in Cardiovascular Diseases, Pharmacol Rev, vol. 54, pp. 619-634, 2002.

Witt et al., CNS Drug Delivery: Opioid Peptides and The Blood-Brain Barrier, The AAPS Journal, vol. 8, No. 1, Article 9, pp. E76-E88, 2006.

\* cited by examiner min  0          3          10

SHORT PEPTIDES USEFUL FOR TREATMENT OF ISCHEMIA/REPERFUSION INJURY AND OTHER TISSUE DAMAGE CONDITIONS ASSOCIATED WITH NITRIC OXIDE AND ITS REACTIVE SPECIES

STATEMENT REGARDING FEDERALLY SPONSORED RESEARCH

Research and development leading to certain aspects of the present invention were supported, in part, by a grant from NIH AI60762. Accordingly, the U.S. government may have certain rights in the invention.

CROSS-REFERENCE TO RELATED APPLICATIONS

This application is a divisional application of U.S. patent application Ser. No. 11/744,104, filed on May 3, 2007, which claims priority under 35 U.S.C. §119, to U.S. Provisional Application Ser. No. 60/887,314, filed on Jan. 30, 2007, the disclosures of both of which are hereby incorporated by reference in their entirety.

TECHNICAL FIELD OF THE INVENTION

This invention relates to isolated short peptides comprising the amino acid sequence Cys-Glu-Phe-His (CEFH; SEQ ID NOS: 1 and 15) and analogs thereof as well as compositions comprising CEFH peptides and analogs thereof. The CEFH peptides disclosed herein are effective in mediating the denitration of 3-nitrotyrosines (3-NT) in cellular proteins thereby preventing tissue damage associated with excess nitric oxide (NO) and its reactive species. Thus, CEFH peptides disclosed herein are useful for treatment of diseases associated with excess NO and its reactive species, which diseases include, but are not limited to, acute and chronic disorders such as ischemia/reperfusion (I/R) injury of various tissues (e.g., I/R injury of heart muscle associated with heart attack or cardiac surgery, I/R injury of brain tissue associated with stroke, I/R injury of liver tissue, skeletal muscles, etc.), septic shock, anaphylactic shock, neurodegenerative diseases (e.g., Alzheimer's and Parkinson's diseases), neuronal injury, atherosclerosis, diabetes, multiple sclerosis, autoimmune uveitis, pulmonary fibrosis, oobliterative bronchiolitis, bronchopulmonary dysplasia (BPD), amyotrophic lateral sclerosis (ALS), sepsis, inflammatory bowel disease, arthritis, allograft rejection, autoimmune myocarditis, myocardial inflammation, pulmonary granulomatous inflammation, influenza- or HSV-induced pneumonia, chronic cerebral vasospasm, allergic encephalomyelitis, central nervous system (CNS) inflammation, *Heliobacterium pylori* gastritis, necrotizing entrerocolitis, celliac disease, peritonitis, early prosthesis failure, inclusion body myositis, preeclamptic pregnancies, skin lesions with anaphylactoid purpura, nephrosclerosis, ileitis, leishmaniasis, cancer, and related disorders.

BACKGROUND OF THE INVENTION

Myocardial infarction is one of the most widespread and serious health problems in Western society. In 2002, in the United States alone, over one million individuals suffered a myocardial infarction with over 25% fatality. During a heart attack, one or more of the arteries that supply the heart becomes blocked by a blood clot, usually at the site of fatty deposits known as arteriosclerosis. When victims are rushed to a hospital, blood flow is restored (the process known as reperfusion) either by drugs that dissolve clots or by angioplasty. Tissue salvage, however, is severely limited by free radicals and inflammatory responses, which cause as much as 80% of the damage during reperfusion (ischemia-reperfusion [I/R] injury). This, in turn, raises the risk of lethality and long-term complications.

A primary outcome of damage resulting from I/R injury is chronic congestive heart failure. Over 22% of male and 46% of female myocardial infarction victims will be disabled with congestive heart failure within six years following their heart attack. As the average age of the population increases and as survival following myocardial infarction improves, congestive heart failure will grow in importance. Following diagnosis of congestive heart failure, prognosis is poor. 12% of patients die within three months of diagnosis, 33% die within one year, and 60% die within five years.

Apart from accidental heart attacks, I/R injury is also a common outcome in cardiac surgery, leading to a spectrum of damage including arrhythmias, post-ischemic myocardial dysfunction, and cardiogenic shock. Furthermore, I/R injury is not limited to heart muscle, and also frequently occurs in the brain (stroke), liver, skeletal muscles and other organs.

Although the mechanism of I/R injury is not fully understood, a large body of evidence implicates a dual role for nitric oxide (NO) in this process. While NO is a potent cardioprotector, its excessive accumulation in ischemic tissue leads to the formation of reactive nitrogen species (e.g., peroxynitrite) that promote tissue injury by nitrating proteins. NO is a signaling molecule that is involved in a multitude of physiological processes including neurotransmission, immune regulation, vascular smooth muscle relaxation, and inhibition of platelet aggregation. See, e.g., Moncada S., *Ann. N.Y. Acad. Sci.* 1997; 811: 60-67; Ischiropoulos H., *Arch Biochem Biophys* 356: 1-11, 1998; Stamler et al., *Cell* 2001; 106: 675-683; Bian et al., J Pharmacol Sci. 2006; 101:271-9.

Depending upon the rate, timing, and spatial distribution of NO production, as well as the chemical microenvironment (e.g., presence of reactive oxygen species and redox status of the cell), NO acts either as a direct signaling messenger or as an indirect toxic effector via the formation of various reactive nitrogen species such as, e.g., peroxynitrite anion ($ONOO^-$) and nitrogen dioxide ($.NO_2$), formed as secondary products of .NO metabolism in the presence of oxidants including superoxide radicals ($O_2.^-$), hydrogen peroxide ($H_2O_2$), and transition metal centers. See Radi, Proc. Natl. Acad. Sci. USA, 2004, 101(12): 4003-4008.

NO is synthesized enzymatically from L-arginine by the enzyme nitric-oxide synthase (NOS) in almost all tissues of the body, including brain, peripheral nervous system, smooth muscle, kidney, vascular, lung, and uterus.

A large body of evidence has established the role of NO in the pathogenesis of inflammatory, infectious, and neurodegenerative diseases. The detrimental role of NO is rooted in the ability of its reactive metabolites to alter the function of biological macromolecules via covalent modifications of protein tyrosine, cysteine and tryptophane amino acid residues.

Cysteines and tryptophanes can be nitrosated to form S—NO and N—NO, respectively. These nitrosoderivatives are readily reversible (and form SH and $NH_2$) in the presence of free thiols.

In contrast, tyrosine nitration has been considered to be an irreversible modification in vivo. Tyrosine nitration is mediated by reactive nitrogen species such as peroxynitrite anion ($ONOO^-$) and nitrogen dioxide ($.NO_2$). Once nitrated at tyrosine, proteins are thus thought to be irreparably damaged. Tyrosine nitration may affect protein structure and lead to loss of protein function or to a constitutively active proteins. For example, nitration of a tyrosine residue may prevent the subsequent phosphorylation of that residue. Alternatively, nitration of tyrosine residues may stimulate phosphorylation and result in constitutively active proteins. Furthermore, tyrosine nitration may change the rate of proteolytic degradation of nitrated proteins and favor either their faster clearance or accumulation in cells. See, e.g., Turko and Murad, Pharmacol. Reviews, 2002, 54(4): 619-634.

3-nitrotyrosine (3-NT) in body fluids and tissues has served as a biomarker of the involvement of NO in acute and chronic disorders such as I/R injury, atherosclerosis, diabetes, septic shock, Alzheimer's disease, Parkinson's disease, multiple sclerosis, pulmonary fibrosis, amyotrophic lateral sclerosis (ALS), inflammatory bowel disease, arthritis, allograft rejection, autoimmune myocarditis, pulmonary granulomatous inflammation, and cancer. Reviewed in, e.g., Ischiropoulos, Arch. Biochem. Biophys., 1998, 356(1): 1-11; Turko and Murad, Pharmacol. Reviews, 2002, 54(4): 619-634; Radi, Proc. Natl. Acad. Sci. USA, 2004, 101(12): 4003-4008.

As previously observed by the present inventors and coworkers (see Rafikova et al., [Abstract] Nitric Oxide: Biology & Chemistry, 2006, 14:A67), tissue NO level is critical in the fate of cardiac tissue during I/R injury. Rats subjected to 30 minutes of myocardial ischemia (MI) and treated with sodium nitrite (5 mg/kg i.v.), infused 1 minute prior to ischemia set up, showed a significant expansion of I/R infarct size and myocardial tissue 3-NT accumulation compared with saline treated controls. In contrast, the use of NOS inhibitor L-NAME (50 mg/kg i.p.) provided the reduction in infarct size and 3-NT. It was also demonstrated that lowering tissue level of NO beyond certain point may also result in an enhanced myocardial damage. Thus, there exists an optimal tissue NO content that provides a minimal cell injury. Larger or smaller amounts of tissue NO are progressively more harmful probably due to either initiation of nitrosative stress or lack of NO antioxidant activity. For example, an excess of NO can lead to the formation of reactive nitrogen species, protein nitration, endothelial dysfunction, PARP and MMP activation, and mitochondrial respiration inhibition. These effects can lead to flow occlusion, apoptosis, necrosis, and inhibition of contractile function. However, a deficit of NO can also lead to detrimental effects since NO is a potent cardioprotector as it, e.g., induces cGMP synthesis, inhibits cytokine expression, and serves as a general antioxidant by intercepting oxygen radicals. As a result, NO in moderate amounts can improve perfusion, inhibit platelet aggregation, inhibit apoptosis, and increase ischemic tolerance.

The majority of current therapies for I/R injury, such as antiplatelet agents, anticoagulants, clot-dissolving drugs, vasodilators, and PTCA, target the occluded coronary artery rather than the ischemic tissue per se. Beta-blockers, which act by decreasing a tissue's $O_2$ demand, are the only commercially available drugs that are protective against I/R damage.

Thus, there remains an unmet need in the art for safe and effective drugs that reduce the tissue damage associated with ischemia/reperfusion (I/R) injury of various tissues as well other types of tissue damage associated with septic shock and neurodegenerative diseases.

SUMMARY OF THE INVENTION

The present invention fulfills these and other related needs by providing isolated short peptides comprising the amino acid sequence Cys-Glu-Phe-His (CEFH; SEQ ID NOS: 1 and 15) as well as analogs and derivatives thereof, which peptides efficiently denitrate cellular proteins and thus prevent tissue damage associated with excess nitric oxide (NO) and its reactive species. The peptides of the invention are characterized by a unique combination of stacking, ionic and hydrophobic interactions that allow them to efficiently transfer the $NO_2$ group from the protein tyrosine to its thiol group and in this way offer an unprecedented level of protection against ischemia/reperfusion (I/R) injury and other conditions associated with excess NO and its reactive species.

The peptides of the present invention are preferably short to allow high accessibility to various parts of a target protein. More preferably, such peptides are less than eight (8) amino acids long, most preferably, such peptides are four (4) amino acids long. Due to their small size, the peptides of the invention can be easily delivered to essentially all tissues and cells of the body, including cells and tissues separated by the blood-brain barrier (BBB).

In a specific embodiment, the peptide of the invention has the sequence Cys-Glu-Phe-His (L-CEFH peptide; SEQ ID NO: 1). In another embodiment, the peptide of the invention has the sequence Cys-Glu-Phe-His and consists of only D-amino acids (D-CEFH peptide). In yet another embodiment, the peptide of the invention has the sequence Cys-Glu-His-His (CEHH peptide; SEQ ID NO: 2). In further embodiments, the peptide has the sequence Cys-Glu-Phe-His-Cys-Glu-Phe-His (CEFH×2 peptide; SEQ ID NO: 3) or contains one or more CEFH peptides fused to one or more CEHH peptides, one or more CEFH peptides fused together, or one or more CEHH peptides fused together. One skilled in the art can envision additional permutations and combinations of the CEFH and CEHH peptides that are within the scope of the present invention, including both linear and cyclic peptides.

In a second embodiment, the invention provides a compound of formula I,

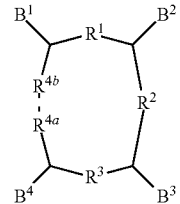

Formula I or a pharmaceutically acceptable salt thereof, wherein the dotted line is a bond or absent; $R^1$, $R^2$, $R^3$ are independently —C(O)NH—, -(AA)$_n$- and —C(O)-(LL)$_n$-NH—; when the dotted line is a bond, $R^{4a}$ and $R^{4b}$ together are —C(O)NH—, -(AA)$_n$- or —C(O)-(LL)$_n$-NH—; when the dotted line is absent, $R^{4a}$ and $R^{4b}$ are not the same and are independently selected from —C(O)OH and —NH$_2$; AA is a natural or unnatural amino acid, LL is a linker selected from —(CH$_2$)$_m$—, —(CH$_2$CH$_2$O)$_m$—, —(CH$_2$CH$_2$S)$_m$— and —(CH$_2$CH$_2$NH)$_m$—, $B^1$, $B^2$, $B^3$ and $B^4$ are not the same and are independently selected from

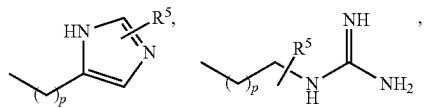

-continued

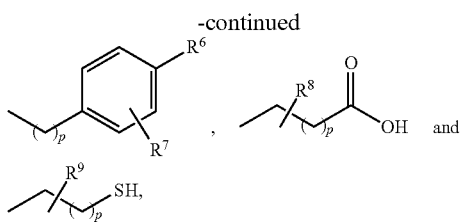

$R^5$, $R^6$, $R^7$, $R^8$ and $R^9$ are independently selected from H, $C_1$-$C_6$ alkyl, halogen, hydroxy, cyano, nitro, nitoso, amino, sulfhydryl, $C_1$-$C_6$ alkoxy, —C(O)O—$C_1$-$C_6$ alkyl, —C(O)O—$C_1$-$C_6$ aryl, substituted or unsusbstituted aryl, substituted or unsubstituted 5 to 7-membered heterocyclic ring, substituted or unsubstituted cycloalkyl, substituted or unsubstituted cycloalkenyl, substituted or unsubstituted arylcarbonyl, substituted or unsubstituted alkylcarbonyl and substituted or unsubstituted aminocarbonylalkyl; each occurrence of n is independently an integer from 0 to 5; each occurrence of m is independently an integer from 1 to 25; and each occurrence of p is independently an integer from 0 to 6.

In another embodiment, $B^1$, $B^2$, $B^3$ and $B^4$ are selected from

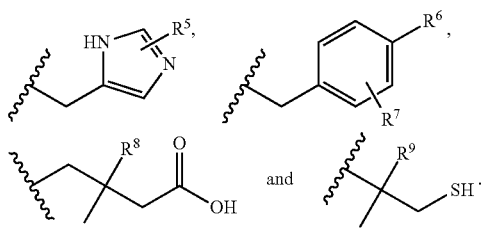

In a further embodiment, $B^1$, $B^2$, $B^3$ and $B^4$ are selected from histidine, phenylalanine, glutamic acid and cysteine In one embodiment $R^1$, $R^2$, $R^3$ and $R^4$ are all peptide bonds and the compound is the cyclic tetrapeptide CEFH (SEQ ID NO: 1).

In another embodiment, one of $R^1$, $R^2$, $R^3$ or $R^4$ is —$NH_2$ and —COOH comprising the N- and C-terminus groups of a linear compound. For example, in the case where $R^1$ is —$NH_2$ and —COOH, the compound is linear tetrapeptide $H_2$N-CEFH—COOH (SEQ ID NO: 1). In the case where $R^2$ is —$NH_2$ and —COOH, the compound is linear tetrapeptide $H_2$N—HCEF-COOH (SEQ ID NO: 4). In the case where $R^3$ is —$NH_2$ and —COOH, the compound is linear tetrapeptide $H_2$N—FHCE-COOH (SEQ ID NO: 5). In the case where $R^4$ is —$NH_2$ and —COOH, the compound is linear tetrapeptide $H_2$N-EFHC—COOH (SEQ ID NO: 6).

In yet another embodiment, $R^1$, $R^2$, $R^3$ or $R^4$ are one or more amino acids. For example, if $R^2$ is alanine the compound is cyclic-CEFAH (SEQ ID NO: 7). If $R^2$ is arginine and $R^3$ is alanine the compound is cyclic-CEAFRH (SEQ ID NO: 8).

In a further embodiment, one or more $R^1$, $R^2$, $R^3$ and $R^4$ can be of a different chemical nature then a peptide bond or an amino acid. For example, the compound may contain an alkyl bridge —$(CH_2)_n$—, polyetheylene glycol —$(CH_2CH_2O)_m$—, —$(CH_2CH_2S)_m$— or —$(CH_2CH_2NH)_m$—, as well as many other derivatives. For example, linkers $R^1$, $R^2$, $R^3$ or $R^4$ may be conjugated with additional molecules in order to achieve a medicinal or pharmacological goal, such as drug targeting and delivery, increasing in vivo lifespan or improved removal from tissues and organs.

In another embodiment, residues $R^5$, $R^6$, $R^7$, $R^8$ and $R^9$ are modified in one or more available positions with functional group that are independently selected from H, $C_1$-$C_6$ alkyl, halogen, hydroxy, cyano, nitro, nitoso, amino, sulfhydryl, $C_1$-$C_6$ alkoxy, —C(O)O—$C_1$-$C_6$ alkyl, —C(O)O—$C_1$-$C_6$ aryl, substituted or unsusbstituted aryl, substituted or unsubstituted 5 to 7-membered heterocyclic ring, substituted or unsubstituted cycloalkyl, substituted or unsubstituted cycloalkenyl, substituted or unsubstituted arylcarbonyl, substituted or unsubstituted alkylcarbonyl and substituted or unsubstituted aminocarbonylalkyl, which may increase denitration activity of the whole molecule.

In a specific embodiment, the amino acid cysteine is replaced with homo-cysteine, histidine is replaced with arginine, phenylalanine is replaced with tyrosine, and glutamic acid is replaced with aspartic acid. Further, any of these amino acids may be substituted with additional chemical groups.

In another embodiment, the relative positions of the amino acid residues may be altered. For example, compounds such as cyclic-CEFH (SEQ ID NOS: 1 or 15), cyclic-CEHF (SEQ ID NO: 9), cyclic-CFEH (SEQ ID NO: 10), cyclic-CFHE (SEQ ID NO: 11), cyclic-CHFE (SEQ ID NO: 12), and cyclic-CHEF (SEQ ID NO: 13) are envisioned.

AA is a natural or unnatural amino acid. In one embodiment, the amino acid is attached via a peptide bond.

The peptides of the present invention can be used at concentrations that are both therapeutically effective and pharmaceutically acceptable. The L-CEFH (SEQ ID NO: 1) peptide of the present invention is preferably used to treat or prevent tissue damage in vivo at 0.1-3.5 mg/kg, most preferably at 0.7 mg/kg. The D-CEFH peptide of the present invention is preferably used at 0.01-0.5 mg/kg, most preferably at 0.1 mg/kg.

Still further aspects of the present invention provide methods for generating and/or identifying novel peptides having the same or better functional characteristics than the CEFH peptides of the invention using the following methods aimed at preserving or improving the unique combination of stacking and/or ionic and/or hydrophobic interactions that allow the CEFH peptides to efficiently mediate the protein tyrosine denitration:

(1) combinatorial shuffling of the relative positions of CEFH amino acids;

(2) addition of a linker (e.g., homocysteine) instead of cysteine (*CEFH) to provide additional spatial flexibility and increase the reach of SH group;

(3) introduction of electropositive substitutions (e.g., $CH_3$, $C_2H_5$, tret-Butyl, etc.) into the benzene ring of phenylalanine (CEF*H);

(4) introduction of tryptophan or cyclic aromatic groups (both natural and synthetic, e.g., naphtalene, tyrosine, and histidine) instead of phenylalanine (CE[F→AR*]H);

(5) substitution of phenylalanine to histidine with or without an electropositive substitution (e.g., $CH_3$, $C_2H_5$, tret-Butyl, etc.) (CE[F→H]H (SEQ ID NO: 2) or (CE[F→H*]H);

(6) modification that increases pKa of glutamic acid (e.g., OH, $NO_2$, or halide in alpha-position) (CE*FH);

(7) substitution of glutamic acid with aspartic acid with or without modifications that increase its pKa (e.g., OH, $NO_2$, or halide in alpha-position) (C[E→D]FH (SEQ ID NO: 14) or C[E→D*]FH).

The present invention further provides in vitro and in vivo methods for functional testing of the novel denitrating peptides generated using the above methods, comprising:

(1) in vitro testing by adding the peptide to a nitrated protein having 3-NT and monitoring the disappearance of 3-NT;

(2) testing by adding the peptide to a cell culture treated with NO and/or reactive NO species (e.g., subject to NO/ONOO-exposure) and measuring cell survival by methods such as, e.g., an MTS-based assay (using the MTS reagent available from Promega, Madison, Wis.) or the direct counting of apoptotic cells using flow cytometry;

(3) testing by adding the peptide to a cell culture treated with NO and/or reactive NO species (e.g., subject to NO/ONOO-exposure) and measuring the disappearance of 3-NT;

(4) in vivo testing by administering the peptide to an animal model of a relevant disease (e.g., I/R injury, septic shock, Alzheimer's disease, etc.) and monitoring the extent of tissue damage and disease progression;

(5) in vivo testing by administering the peptide to an animal model for I/R injury and determining the size of the infarct using a p-nitro-blue tetrazolium (NBT)-based assay while also monitoring functional parameters such as heart rate, mean arterial blood pressure, cardiac output, etc.

Useful compounds of the present invention are not limited to peptides incorporating natural and/or non-natural amino acids. A number of non-peptide molecules having similar functional properties can be developed to incorporate disparate chemical functional groups within a single molecule. Chemical functionality comprising these molecules as well as peptides of the invention would include (i) at least one thiol group (for example, cysteine or homocysteine), (ii) at least one polar group (for example, a functional group with a measurable dipole moment, including, but not limited to, carbonyl groups such as in ketones, esters, or amides, imine groups alone or in heterocycles, cyano groups, guanidine groups, amidine groups, etc. as in serine, threonine, lysine, arginine, histidine, tyrosine, tryptophan, glutamic acid, aspartic acid, glutamine or asparagine, cysteine or methionine), (iii) at least one proton donor (such as an alcohol, carboxylic acid, hydroxyl amine, heterocyclic or heteroaromatic NH or OH as in serine, threonine, lysine, arginine, histidine, tyrosine, tryptophan, glutamic acid, aspartic acid, glutamine or asparagine), and (iv) at least one aromatic group (for example, carbocyclic or heteroaromatic groups as in tyrosine, tryptophan, histidine or phenylalanine). It is envisioned that these chemical groups may be combined into a single functional group (for example tyrosine, tryptophan, histidine, glutamic acid, aspartic acid, glutamine, asparagine, arginine, and lysine) or be comprised in different portions of the molecule.

The present invention also provides compositions comprising one or more compounds of the invention and a pharmaceutically acceptable carrier, excipient, and/or diluent. Such compositions may further comprise additional active ingredients having a cumulative effect such as small thiols (e.g., lipoic acid, homocysteine, N-acetylcysteine [NAC], thioredoxin [TRX], and Bucillamine).

In conjunction with these compounds and compositions, the present invention provides methods for use of such compounds and compositions to (i) stimulate denitration of 3-nitrotyrosine in a cell or tissue of an animal, (ii) prevent cell death induced by nitric oxide and its reactive species, (iii) prevent ischemia-reperfusion injury in a tissue of an animal, and/or (iv) treat a disorder manifested by accumulation of 3-nitrotyrosine in an animal, including, but not limited to, tissue damage associated with I/R injury of various tissues (e.g., I/R injury of heart muscle associated with heart attack or cardiac surgery, I/R injury of brain tissue associated with stroke, I/R injury of liver tissue, skeletal muscles, etc.), septic shock, anaphylactic shock, neurodegenerative diseases (e.g., Alzheimer's and Parkinson's diseases), neuronal injury, atherosclerosis, diabetes, multiple sclerosis, autoimmune uveitis, pulmonary fibrosis, oobliterative bronchiolitis, bronchopulmonary dysplasia (BPD), amyotrophic lateral sclerosis (ALS), sepsis, inflammatory bowel disease, arthritis, allograft rejection, autoimmune myocarditis, myocardial inflammation, pulmonary granulomatous inflammation, influenza- or HSV-induced pneumonia, chronic cerebral vasospasm, allergic encephalomyelitis, central nervous system (CNS) inflammation, *Heliobacterium pylori* gastritis, necrotizing entrerocolitis, celliac disease, peritonitis, early prosthesis failure, inclusion body myositis, preeclamptic pregnancies, skin lesions with anaphylactoid purpura, nephrosclerosis, ileitis, leishmaniasis, cancer, and related disorders. In related aspects, the present invention provides isolated polynucleotides that encode the peptides of the present invention as well as recombinant vectors and host cells (both eukaryotic and prokaryotic) that have been genetically modified to express or overexpress the peptides of the present invention.

In a separate embodiment, the present invention provides a method for treating ischemia/reperfusion (I/R) injury and treating/reducing in vitro and in vivo other types of tissue damage associated with the diseases mentioned above by exposing nitrated proteins to excess of small thiols. Examples of small thiols useful in the methods of the invention include, without limitation, homocysteine, N-acetylcysteine [NAC], lipoic acid, thioredoxin [TRX], and Bucillamine. The present invention also provides combination treatments using peptides of the invention and small thiols.

These and other aspects of the present invention will become apparent upon reference to the following detailed description and attached drawings. All publications, patents, and patent applications cited herein, whether supra or infra, are hereby incorporated by reference in their entirety.

DETAILED DESCRIPTION OF THE INVENTION

Figure 1:
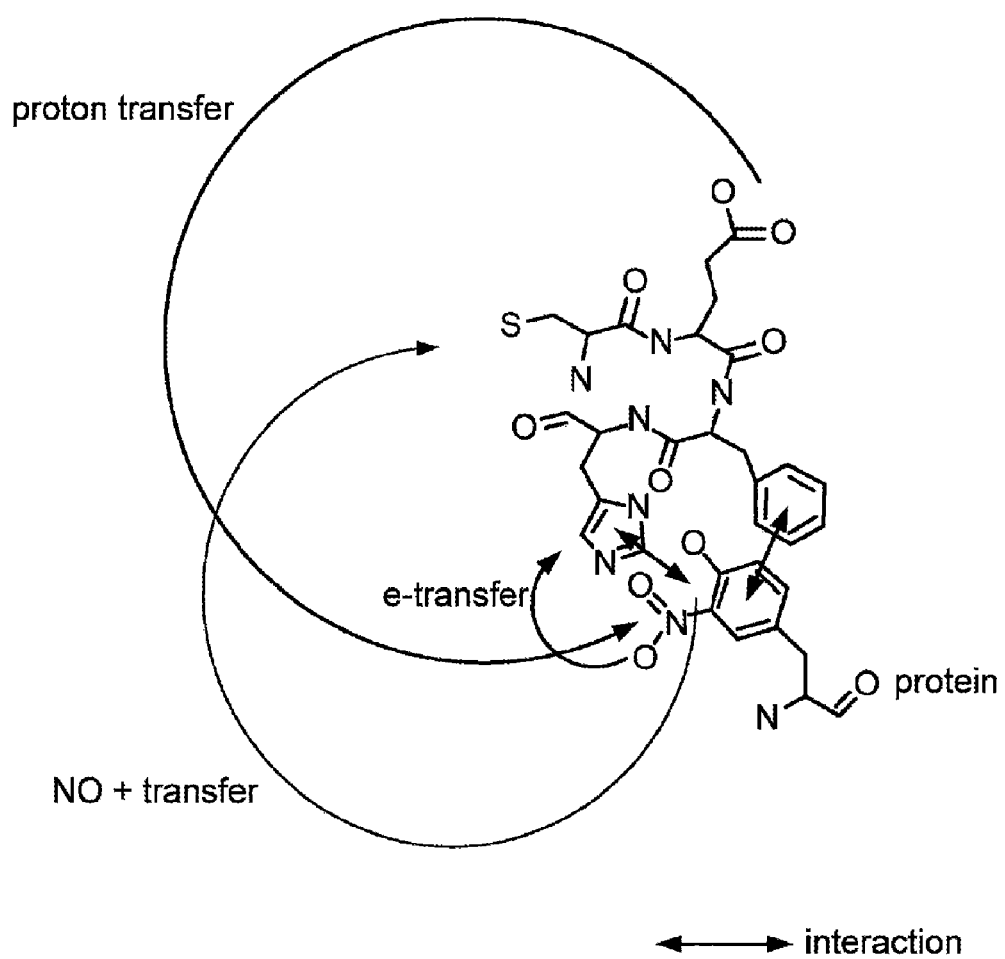
FIG. 1 schematically shows interaction of the L-CEFH (SEQ ID NO: 1) peptide with protein 3-NT. The chemical structure of the peptide is shown in bold. The scheme shows how a unique combination of stacking, ionic and hydrophobic interactions allow the peptides of the present invention to efficiently transfer the $NO_2$ group from the protein tyrosine to its thiol group.

As specified in the Background Section, 3-NT in body fluids and tissues is a biomarker of the involvement of NO in acute and chronic disorders such as I/R injury, atherosclerosis, diabetes, septic shock, Alzheimer's disease, Parkinson's disease, multiple sclerosis, pulmonary fibrosis, amyotrophic lateral sclerosis (ALS), inflammatory bowel disease, arthritis, allograft rejection, autoimmune myocarditis, pulmonary granulomatous inflammation, and cancer. Reviewed in, e.g., Ischiropoulos, Arch. Biochem. Biophys., 1998, 356(1): 1-11; Turko and Murad, Pharmacol. Reviews, 2002, 54(4): 619-634; Radi, Proc. Natl. Acad. Sci. USA, 2004, 101(12): 4003-4008.

The present invention provides isolated short peptides comprising the amino acid sequence Cys-Glu-Phe-His (CEFH; SEQ ID NOS: 1 and 15) as well as analogs and derivatives thereof, which peptides efficiently denitrate cellular proteins and thus prevent tissue damage associated with excess nitric oxide (NO) and its reactive species. The peptides of the invention are characterized by a unique combination of stacking, ionic and hydrophobic interactions that allow them to efficiently transfer the $NO_2$ group from the protein tyrosine to its thiol group and in this way offer an unprecedented level of protection against I/R injury and other conditions associated with excess NO and its reactive species.

In a separate embodiment, the present invention provides a method for treating I/R injury and other conditions associated with excess NO and its reactive species by exposing nitrated proteins to excess of small thiols. Examples of small thiols useful in the methods of the invention include, without limitation, homocysteine, N-acetylcysteine [NAC], lipoic acid, thioredoxin [TRX], and Bucillamine. The present invention also provides combination treatments using peptides of the invention and small thiols.

The short peptides, small thiols, and compositions of the invention have utility over a wide range of therapeutic applications, and may be used to treat various types of tissue damage associated with NO and its reactive species. More specifically, the compounds and compositions of this invention may be used to treat disorders including but not limited to tissue damage associated with I/R injury of various tissues (e.g., I/R injury of heart muscle associated with heart attack or cardiac surgery, I/R injury of brain tissue associated with stroke, I/R injury of liver tissue, skeletal muscles, etc.), septic shock, anaphylactic shock, neurodegenerative diseases (e.g., Alzheimer's and Parkinson's diseases), neuronal injury, atherosclerosis, diabetes, multiple sclerosis, autoimmune uveitis, pulmonary fibrosis, oobliterative bronchiolitis, bronchopulmonary dysplasia (BPD), amyotrophic lateral sclerosis (ALS), sepsis, inflammatory bowel disease, arthritis, allograft rejection, autoimmune myocarditis, myocardial inflammation, pulmonary granulomatous inflammation, influenza- or HSV-induced pneumonia, chronic cerebral vasospasm, allergic encephalomyelitis, central nervous system (CNS) inflammation, *Heliobacterium pylori* gastritis, necrotizing entrerocolitis, celliac disease, peritonitis, early prosthesis failure, inclusion body myositis, preeclamptic pregnancies, skin lesions with anaphylactoid purpura, nephrosclerosis, ileitis, leishmaniasis, cancer, and related disorders The practice of the present invention will employ, unless indicated specifically to the contrary, conventional methods of molecular biology, cell biology and protein chemistry within the skill of the art, many of which are described below for the purpose of illustration. Such techniques are explained fully in the literature. See, e.g., Sambrook, et al., "Molecular Cloning: A Laboratory Manual" (2nd Edition, 1989); "DNA Cloning: A Practical Approach, vol. I & II" (D. Glover, ed.); "Oligonucleotide Synthesis" (N. Gait, ed., 1984); "Nucleic Acid Hybridization" (B. Hames & S. Higgins, eds., 1985); Perbal, "A Practical Guide to Molecular Cloning" (1984); Ausubel et al., "Current protocols in Molecular Biology" (New York, John Wiley and Sons, 1987); and Bonifacino et al., "Current Protocols in Cell Biology" (New York, John Wiley & Sons, 1999).

DEFINITIONS

As used herein, the term "CEFH peptide" is used to refer to any peptide of the invention comprising the sequence Cys-Glu-Phe-His (SEQ ID NOS: 1 and 15) or any analog or derivative thereof.

As used herein, the term "amino acid" is used to refer to any molecule containing an amine and a carboxylic acid. In one embodiment, the amino acid is attached via a peptide bond.

As used herein in connection with the peptides of the invention, the terms "peptide derivatives" and "peptide analogs" are used interchangeably to refer to peptides in which one or more amino acid residues have been substituted or modified in order (i) to preserve or improve the unique combination of stacking and/or ionic and/or hydrophobic interactions that allow the CEFH peptides to efficiently denitrate and/or denitrosylate cellular proteins, and/or (ii) to preserve or improve the delivery of the peptide of the invention to the cells and tissues requiring protein denitration. Peptide derivatives and analogs according to the present invention include, without limitation, (1) peptides having one or several amino acid replacements with amino acids or non-natural amino acid analogs having similar properties (such as, for example, polarity, hydrogen bonding potential, acidic, basic, hydrophobic, aromatic, and the like); (2) peptides produced by combinatorial shuffling of the relative positions of CEFH amino acids to attain spatial arrangements of the catalysis components that are more active than in CEFH peptides; (3) peptides produced by addition of a linker (e.g., homocysteine) instead of cysteine (*CEFH) to provide additional spatial flexibility and increase the reach of SH group as an acceptor of NO; (4) peptides produced by introduction of electropositive substitutions (e.g., CH₃, C₂H₅, tret-Butyl, etc.) into the benzene ring of phenylalanine (CEF*H) to increase the stacking interaction between protein 3-NT and phenylalanine; (5) peptides produced by introduction of tryptophan or cyclic aromatic groups (both natural and synthetic, e.g., naphtalene, tyrosine, and histidine) instead of phenylalanine (CE[F→AR*]H) to stabilize the stacking interaction with protein 3-NT because of two conjugated aromatic rings; (6) peptides produced by substitution (e.g., of phenylalanine) with histidine with or without an electropositive substitution (e.g., CH₃, C₂H₅, tret-Butyl, etc.) (CE[F→H]H (SEQ ID NO: 2) or (CE[F→H*]H)) to increase the efficiency of denitration of the tyrosine in the protein; (7) peptides produced by modifications that increase pKa of glutamic acid (e.g., OH, NO₂, or halide in alpha-position) (CE*FH) to increase the rate of denitration; (8) substitution of glutamic acid with aspartic acid with or without modifications that increase its pKa (e.g., OH, NO₂, or halide in alpha-position) (C[E→D]FH (SEQ ID NO: 14) or C[E→D*]FH); (9) peptides produced by additions or substitutions that increase the overall hydrophobicity of the peptide and thus render it more cell- and protein globule-permeable.

The term "linker" means any chemical group positioned between the amino acid segments of the compounds of the present invention. These chemical groups may be of any stable chemical structure, and may provide spacing between segments, impart conformational constraints on the segments, provide drug targeting or drug delivery functionality, increase absorption and/or lifespan in vivo, or provide any additional ancillary role that benefits the utility of the molecule. Examples include, but are not limited to, methylene —(CH₂)$_n$— units, polyethylene glycol or other bioploymeric molecules, sugar or carbohydrate moieties, natural products, peptide-nucleic acid (PNA) molecules, both natural and unnatural amino acids and nucleic acids.

Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, —COOR$_x$, —C(O)R$_x$, —C(S)R$_x$, —C(O)NR$_x$R$_y$, —C(O)ONR$_x$R$_y$, —NR$_x$CONR$_y$R$_z$, —N(R$_x$) SOR$_y$, —N(R$_x$)SO₂R$_y$, —(=N—N(R$_x$)R$_y$), —NR$_x$C(O) OR$_y$, —NR$_x$R$_y$, —NR$_x$C(O)R$_y$, —NR$_x$C(S)R$_y$, —NR$_x$C(S) NR$_y$R$_z$, —SONR$_x$R$_y$, —SO₂NR$_x$R$_y$, —OR$_x$, —OR$_x$C(O) NR$_y$R$_z$, —OR$_x$C(O)OR$_y$, —OC(O)R$_x$, —OC(O)NR$_x$R$_y$, —R$_x$NR$_y$C(O)R$_z$, —R$_x$OR$_y$, —R$_x$C(O)OR$_y$, —R$_x$C(O) NR$_y$R$_z$, —R$_x$C(O)R$_y$, —R$_x$OC(O)R$_y$, —SR$_x$, —SOR$_x$, —SO₂R$_x$, and —ONO₂, wherein R$_x$, R$_y$ and R$_z$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. According to one embodiment, the substituents in the aforementioned "substituted" groups cannot be further substituted. For example, when the substituent on "substituted alkyl" is "substituted aryl" the substituent on "substituted aryl" cannot be "substituted alkenyl".

The phrases "reactive species of nitric oxide" or "reactive NO species" mean the chemicals capable of nitrosation and nitration of target macromolecules, e.g. N₂O₃, N₂O₄, ONOO—, and .NO₂. Peroxynitrite anion (ONOO⁻) and nitrogen dioxide (.NO₂), are formed as secondary products of .NO metabolism in the presence of oxidants including superoxide radicals (O₂.⁻), hydrogen peroxide (H₂O₂), and transition metal centers.

The term "thiol" is used to refer to molecules containing sulfhydryl (—SH) groups that play a role in maintaining the body's redox balance and defense against oxidants. Examples of small thiols useful in the methods of the present invention include, without limitation, lipoic acid, homocysteine, N-acetylcysteine (NAC), thioredoxin (TRX), and Bucillamine.

As used herein, the term "isolated" means that the material being referred to has been removed from the environment in which it is naturally found, and is characterized to a sufficient degree to establish that it is present in a particular sample. Such characterization can be achieved by any standard technique, such as, e.g., sequencing, hybridization, immunoassay, functional assay, expression, size determination, or the like. Thus, a biological material can be "isolated" if it is free of cellular components, i.e., components of the cells in which the material is found or produced in nature. A protein or peptide that is associated with other proteins and/or nucleic acids with which it is associated in an intact cell, or with cellular membranes if it is a membrane-associated protein, is considered isolated if it has otherwise been removed from the environment in which it is naturally found and is characterized to a sufficient degree to establish that it is present in a particular sample. A protein or peptide expressed from a recombinant vector in a host cell, particularly in a cell in which the protein is not naturally expressed, is also regarded as isolated.

An isolated organelle, cell, or tissue is one that has been removed from the anatomical site (cell, tissue or organism) in which it is found in the source organism. An isolated material may or may not be "purified". The term "purified" as used herein refers to a material (e.g., a nucleic acid molecule or a protein) that has been isolated under conditions that detectably reduce or eliminate the presence of other contaminating materials. Contaminants may or may not include native materials from which the purified material has been obtained. A purified material preferably contains less than about 90%, less than about 75%, less than about 50%, less than about 25%, less than about 10%, less than about 5%, or less than about 2% by weight of other components with which it was originally associated.

Methods for purification are well-known in the art. For example, polypeptides can be purified by various methods including, without limitation, preparative disc-gel electrophoresis, isoelectric focusing, HPLC, reverse-phase HPLC, gel filtration, affinity chromatography, ion exchange and partition chromatography, precipitation and salting-out chromatography, extraction, and counter-current distribution. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting (FACS)). Other purification methods are possible.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In the context of the present invention insofar as it relates to any of the disease conditions recited herein, the terms "treat", "treatment", and the like mean to relieve or alleviate at least one symptom associated with such condition, or to slow or reverse the progression of such condition. For example, in relation to ischemia/reperfusion (I/R) injury of various tissues, septic shock, anaphylactic shock, neurodegenerative diseases (e.g., Alzheimer's and Parkinson's diseases), neuronal injury, atherosclerosis, diabetes, multiple sclerosis, autoimmune uveitis, pulmonary fibrosis, oobliterative bronchiolitis, bronchopulmonary dysplasia (BPD), amyotrophic lateral sclerosis (ALS), sepsis, inflammatory bowel disease, arthritis, allograft rejection, autoimmune myocarditis, myocardial inflammation, pulmonary granulomatous inflammation, influenza- or HSV-induced pneumonia, chronic cerebral vasospasm, allergic encephalomyelitis, central nervous system (CNS) inflammation, *Heliobacterium pylori* gastritis, necrotizing entrerocolitis, celliac disease, peritonitis, early prosthesis failure, inclusion body myositis, preeclamptic pregnancies, skin lesions with anaphylactoid purpura, nephrosclerosis, ileitis, leishmaniasis, and cancer treated by the compounds of the present invention, the term "treat" may mean to relieve or alleviate at least one symptom of tissue damage selected from the group consisting of cellular apoptosis, cellular necrosis, cellular transformation, cellular dysfunction etc. Methods for detecting these symptoms of tissue damage are well known in the art. For example, as disclosed in the Examples section, below, apoptosis can be detected using an MTS-based assay (using the MTS reagent available from Promega, Madison, Wis.) or the direct counting of apoptotic cells using flow cytometry. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent, delay or treat, or all, as appropriate, development or continuance or aggravation of a disease in a subject. Within the meaning of the present invention, disease conditions include without limitation ischemia/reperfusion (I/R) injury of various tissues (e.g., I/R injury of heart muscle associated with heart attack or cardiac surgery, I/R injury of brain tissue associated with stroke, I/R injury of liver tissue, skeletal muscles, etc.), septic shock, anaphylactic shock, neurodegenerative diseases (e.g., Alzheimer's and Parkinson's diseases), neuronal injury, atherosclerosis, diabetes, multiple sclerosis, autoimmune uveitis, pulmonary fibrosis, oobliterative bronchiolitis, bronchopulmonary dysplasia (BPD), amyotrophic lateral sclerosis (ALS), sepsis, inflammatory bowel disease, arthritis, allograft rejection, autoimmune myocarditis, myocardial inflammation, pulmonary granulomatous inflammation, influenza- or HSV-induced pneumonia, chronic cerebral vasospasm, allergic encephalomyelitis, central nervous system (CNS) inflammation, *Heliobacterium pylori* gastritis, necrotizing entrerocolitis, celliac disease, peritonitis, early prosthesis failure, inclusion body myositis, preeclamptic pregnancies, skin lesions with anaphylactoid purpura, nephrosclerosis, ileitis, leishmaniasis, cancer, and related diseases.

As used herein, the phrase "reduce tissue damage" means reduction of the necrotic and/or apoptotic area associated with cytotoxic stress, e.g. oxidative stress, inflammation, hypoxia etc. A "significant reduction in tissue damage" is a reduction of at least about 10% compared to an appropriate control. As used herein the term "therapeutically effective" applied to dose or amount refers to that quantity of a compound or pharmaceutical composition that is sufficient to result in a desired activity upon administration to an animal in need thereof. Within the context of the present invention, the term "therapeutically effective" refers to that quantity of a compound or pharmaceutical composition that is sufficient to reduce or eliminate at least one symptom of tissue damage selected from the group consisting of cellular apoptosis, cellular necrosis, etc. Methods for detecting these symptoms of tissue damage are well known in the art. Note that when a combination of active ingredients is administered the effective amount of the combination may or may not include amounts of each ingredient that would have been effective if administered individually.

The phrase "pharmaceutically acceptable", as used in connection with compositions of the invention, refers to molecular entities and other ingredients of such compositions that are physiologically tolerable and do not typically produce untoward reactions when administered to an animal such as a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans. "Pharmaceutically acceptable" can also mean concentrations of the CEFH peptide that do not reduce the concentration of nitrated/nitrosated proteins below a level required to maintain normal heart function.

The terms "administering" or "administration" are intended to encompass all means for directly and indirectly delivering a compound to its intended site of action. The compounds of the present invention can be administered locally to the affected site (e.g., by direct injection into the affected tissue) or systemically. The term "systemic" as used herein includes parenteral, topical, oral, spray inhalation, rectal, nasal, and buccal administration. Parenteral administration includes subcutaneous, intravenous, intramuscular, intra-articular, intra-synovial, intrasternal, intrathecal, intrahepatic, intralesional, and intracranial administration.

The term "animal" means any animal, including mammals and, in particular, humans.

As used in this specification and the appended claims, the singular forms "a," "an," and "the" include plural references unless the context clearly dictates otherwise.

Compounds of the Invention

The present invention provides isolated short peptides comprising the amino acid sequence Cys-Glu-Phe-His (CEFH; SEQ ID NOS: 1 and 15) as well as analogs and derivatives thereof, which peptides efficiently denitrate cellular proteins and thus prevent tissue damage associated with excess nitric oxide (NO) and its reactive species. The peptides of the invention are characterized by a unique combination of stacking, ionic and hydrophobic interactions that allow them to efficiently transfer the NO$_2$ group from the protein tyrosine to its thiol group and in this way offer an unprecedented level of protection against I/R injury and other conditions associated with excess NO and its reactive species.

The peptides of the present invention are preferably short to allow high accessibility to various parts of a target protein. More preferably, such peptides are less than eight (8) amino acids long, most preferably, such peptides are four (4) amino acids long. Due to their small size, the peptides of the invention can be easily delivered to essentially all tissues and cells of the body, including cells and tissues separated by the blood-brain barrier (BBB).

In a specific embodiment, the peptide of the invention has the sequence Cys-Glu-Phe-His (L-CEFH peptide; SEQ ID NO: 1). In another embodiment, the peptide of the invention has the sequence Cys-Glu-Phe-His and consists of only D-amino acids (D-CEFH peptide). In yet another embodiment, the peptide of the invention has the sequence Cys-Glu-His-His (CEHH peptide; SEQ ID NO: 2). In further embodiments, the peptide has the sequence Cys-Glu-Phe-His-Cys-Glu-Phe-His (CEFHx2 peptide; SEQ ID NO: 3) or contains one or more CEFH peptides fused to one or more CEHH peptides, one or more CEFH peptides fused together, or one or more CEHH peptides fused together. One skilled in the art can envision additional permutations and combinations of the CEFH and CEHH peptides that are within the scope of the present invention, including both linear and cyclic peptides.

In a second embodiment, the invention provides a compound of formula I,

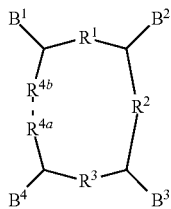

Formula I or a pharmaceutically acceptable salt thereof, wherein the dotted line is a bond or absent; $R^1$, $R^2$, $R^3$ and $R^4$ are independently —C(O)NH—, -(AA)$_n$- and —C(O)-(LL)$_n$-NH—; when the dotted line is a bond, $R^{4a}$ and $R^{4b}$ together are —C(O)NH—, -(AA)$_n$- or —C(O)-(LL)$_n$-NH—; when the dotted line is absent, $R^{4a}$ and $R^{4b}$ are not the same and are independently selected from —C(O)OH and —NH$_2$; AA is a natural or unnatural amino acid, LL is a linker selected from —(CH$_2$)$_m$—, —(CH$_2$CH$_2$O)$_m$—, —(CH$_2$CH$_2$S)$_m$— and —(CH$_2$CH$_2$NH)$_m$—, $B^1$, $B^2$, $B^3$ and $B^4$ are not the same and are independently selected from

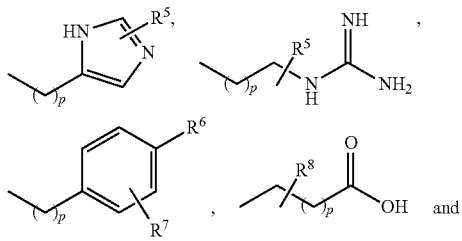

$R^5$, $R^6$, $R^7$, $R^8$ and $R^9$ are independently selected from H, $C_1$-$C_6$ alkyl, halogen, hydroxy, cyano, nitro, nitoso, amino, sulfhydryl, $C_1$-$C_6$ alkoxy, —C(O)O—$C_1$-$C_6$ alkyl, —C(O)O—$C_1$-$C_6$ aryl, substituted or unsusbstituted aryl, substituted or unsubstituted 5 to 7-membered heterocyclic ring, substituted or unsubstituted cycloalkyl, substituted or unsubstituted cycloalkenyl, substituted or unsubstituted arylcarbonyl, substituted or unsubstituted alkylcarbonyl and substituted or unsubstituted aminocarbonylalkyl; each occurrence of n is independently an integer from 0 to 5; each occurrence of m is independently an integer from 1 to 25; and each occurrence of p is independently an integer from 0 to 6.

In another embodiment, $B^1$, $B^2$, $B^3$ and $B^4$ are selected from

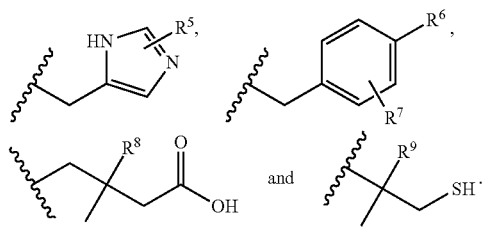

In a further embodiment, $B^1$, $B^2$, $B^3$ and $B^4$ are selected from histidine, phenylalanine, glutamic acid and cysteine.

In one embodiment $R^1$, $R^2$, $R^3$ and $R^4$ are all peptide bonds and the compound is the cyclic tetrapeptide CEFH (SEQ ID NO: 1).

In another embodiment, one of $R^1$, $R^2$, $R^3$ or $R^4$ is —NH$_2$ and —COOH comprising the N- and C-terminus groups of a linear compound. For example, in the case where $R^1$ is —NH$_2$ and —COOH, the compound is linear tetrapeptide H$_2$N-CEFH—COOH (SEQ ID NO: 1). In the case where $R^2$ is —NH$_2$ and —COOH, the compound is linear tetrapeptide H$_2$N—HCEF-COOH (SEQ ID NO: 4). In the case where $R^3$ is —NH$_2$ and —COOH, the compound is linear tetrapeptide H$_2$N—FHCE-COOH (SEQ ID NO: 5). In the case where $R^4$ is —NH$_2$ and —COOH, the compound is linear tetrapeptide H$_2$N-EFHC—COOH (SEQ ID NO: 6).

In yet another embodiment, $R^1$, $R^2$, $R^3$ or $R^4$ are one or more amino acids. For example, if $R^2$ is alanine the compound is cyclic-CEFAH (SEQ ID NO: 7). If $R^2$ is arginine and $R^3$ is alanine the compound is cyclic-CEAFRH (SEQ ID NO: 8).

In a further embodiment, one or more $R^1$, $R^2$, $R^3$ and $R^4$ can be of a different chemical nature then a peptide bond or an amino acid. For example, the compound may contain an alkyl bridge —(CH$_2$)$_n$—, polyetheylene glycol —(CH$_2$CH$_2$O)$_m$—, —(CH$_2$CH$_2$S)$_m$— or —(CH$_2$CH$_2$NH)$_m$—, as well as many other derivatives. For example, linkers $R^1$, $R^2$, $R^3$ or $R^4$ may be conjugated with additional molecules in order to achieve a medicinal or pharmacological goal, such as drug targeting and delivery, increasing in vivo lifespan or improved removal from tissues and organs.

In another embodiment, residues $R^5$, $R^6$, $R^7$, $R^8$ and $R^9$ are modified in one or more available positions with functional group that are independently selected from H, $C_1$-$C_6$ alkyl, halogen, hydroxy, cyano, nitro, nitoso, amino, sulfhydryl, $C_1$-$C_6$ alkoxy, —C(O)O—$C_1$-$C_6$ alkyl, —C(O)O—$C_1$-$C_6$ aryl, substituted or unsusbstituted aryl, substituted or unsubstituted 5 to 7-membered heterocyclic ring, substituted or unsubstituted cycloalkyl, substituted or unsubstituted cycloalkenyl, substituted or unsubstituted arylcarbonyl, substituted or unsubstituted alkylcarbonyl and substituted or unsubstituted aminocarbonylalkyl, which may increase denitration activity of the whole molecule.

In a specific embodiment, the amino acid cysteine is replaced with homo-cysteine, histidine is replaced with arginine, phenylalanine is replaced with tyrosine, and glutamic acid is replaced with aspartic acid. Further, any of these amino acids may be substituted with additional chemical groups.

In another embodiment, the relative positions of the amino acid residues may be altered. For example, compounds such as cyclic-CEFH (SEQ ID NOS: 1 and 15), cyclic-CEHF (SEQ ID NO: 9), cyclic-CFEH (SEQ ID NO: 10), cyclic-CFHE (SEQ ID NO: 11), cyclic-CHFE (SEQ ID NO: 12), and cyclic-CHEF (SEQ ID NO: 13) are envisioned.

AA is a natural or unnatural amino acid. In one embodiment, the amino acid is attached via a peptide bond.

Modified Peptides of the Invention

The peptides of the invention can be modified in various ways to improve their pharmacokinetic and other properties. Peptides can be modified at the amino (N—) terminus, and/or carboxy (C—) terminus and/or by replacement of one or more of the naturally occurring genetically encoded amino acids with an unconventional amino acid, modification of the side chain of one or more amino acid residues, peptide phosphorylation, and the like.

Amino terminus modifications include methylation (e.g., —NHCH$_3$ or —N(CH$_3$)$_2$), acetylation (e.g., with acetic acid or a halogenated derivative thereof such as α-chloroacetic acid, α-bromoacetic acid, or α-iodoacetic acid), adding a benzyloxycarbonyl (Cbz) group, or blocking the amino terminus with any blocking group containing a carboxylate functionality defined by RCOO— or sulfonyl functionality defined by R—SO$_2$—, where R is selected from alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound.

Carboxy terminus modifications include replacing the free acid with a carboxamide group or forming a cyclic lactam at the carboxy terminus to introduce structural constraints. One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the 20 genetically encoded amino acids (or the stereoisomeric D-amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. For example, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

Common examples of conventional amino acid replacements include stereoisomers (e.g., D-amino acids) and unnatural amino acids such as, for example, L-ornithine, L-homocysteine, L-homoserine, L-citrulline, 3-sulfino-L-alanine, N-(L-arginino)succinate, 3,4-dihydroxy-L-phenylalanine, 3-iodo-L-tyrosine, 3,5-diiodo-L-tyrosine, triiodothyronine, L-thyroxine, L-selenocysteine, N-(L-arginino) taurine, 4-aminobutylate, (R,S)-3-amino-2-methylpropanoate, a,a-disubstituted amino acids, N-alkyl amino acids, lactic acid, β-alanine, 3-pyridylalanine, 4-hydroxyproline, O-phosphoserine, N-methylglycine, N-acetylserine, N-formylmethionine, 3-methylhistidine, 5-hydroxylysine, nor-leucine, and other similar amino acids and imino acids. A general method for site-specific incorporation of unnatural amino acids into proteins and peptides is described in Noren et al., Science, 244:182-188 (April 1989).

One can also readily modify peptides by phosphorylation, and other methods (e.g., as described in Hruby, et al. (1990) Biochem J. 268:249-262).

The peptide compounds of the invention also serve as structural models for non-peptidic compounds with similar biological activity. Those of skill in the art recognize that a variety of techniques are available for constructing compounds with the same or similar desired biological activity as the lead peptide compound, but with more favorable activity than the lead with respect to solubility, stability, and susceptibility to hydrolysis and proteolysis (see, e.g., Morgan and Gainor (1989) Ann. Rep. Med. Chem. 24:243-252). These techniques include replacing the peptide backbone with a backbone composed of phosphonates, amidates, carbamates, sulfonamides, secondary amines, and N-methylamino acids.

The present invention also provides conjugates of the disclosed peptide monomers. Thus, according to a preferred embodiment, the monomeric peptides of the present invention are dimerized or oligomerized, thereby enhancing their biological activity.

In one embodiment, the peptide monomers of the invention may be oligomerized using the biotin/streptavidin system. Biotinylated analogs of peptide monomers may be synthesized by standard techniques. For example, the peptide monomers may be C-terminally biotinylated. These biotinylated monomers are then oligomerized by incubation with streptavidin [e.g., at a 4:1 molar ratio at room temperature in phosphate buffered saline (PBS) or HEPES-buffered RPMI medium (Invitrogen) for 1 hour]. In a variation of this embodiment, biotinylated peptide monomers may be oligomerized by incubation with any one of a number of commercially available anti-biotin antibodies [e.g., goat anti-biotin IgG from Kirkegaard & Perry Laboratories, Inc. (Washington, D.C.)].

Linkers.

In other embodiments, the peptide monomers of the invention can be dimerized by covalent attachment to at least one linker moiety. The linker ($L_K$) moiety can be a $C_{1-12}$ linking moiety optionally terminated with one or two —NH— linkages and optionally substituted at one or more available carbon atoms with a lower alkyl substituent (e.g., —NH—R—NH— wherein R is a lower ($C_{1-6}$) alkylene substituted with a functional group such as a carboxyl group or an amino group, such as, for example, a lysine residue or a lysine amide).

In an additional embodiment, polyethylene glycol (PEG) may serve as the linker $L_K$ that dimerizes two peptide monomers: for example, a single PEG moiety may be simultaneously attached to the N-termini of both peptide chains of a peptide dimer.

In yet another additional embodiment, the linker ($L_K$) moiety is preferably, but not necessarily, a molecule containing two carboxylic acids and optionally substituted at one or more available atoms with an additional functional group such as an amine capable of being bound to one or more PEG molecules. Such a molecule can be depicted as:

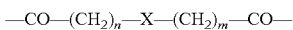

where n is an integer from 0 to 10, m is an integer from 1 to 10, X is selected from O, S, N($CH_2$)$_p$$NR_1$, NCO($CH_2$)$_p$$NR_1$, and $CHNR_1$, $R_1$ is selected from H, Boc, Cbz, etc., and p is an integer from 1 to 10.

Linkers can be incorporated into the peptide during peptide synthesis. For example, where a linker $L_K$ moiety contains two functional groups capable of serving as initiation sites for peptide synthesis and a third functional group (e.g., a carboxyl group or an amino group) that enables binding to another molecular moiety, the linker may be conjugated to a solid support. Thereafter, two peptide monomers may be synthesized directly onto the two reactive nitrogen groups of the linker $L_K$ moiety in a variation of the solid phase synthesis technique.

In alternate embodiments where a peptide dimer is dimerized by a linker $L_K$ moiety, said linker may be conjugated to the two peptide monomers of a peptide dimer after peptide synthesis. Such conjugation may be achieved by methods well established in the art. In one embodiment, the linker contains at least two functional groups suitable for attachment to the target functional groups of the synthesized peptide monomers. For example, a linker with two free amine groups may be reacted with the C-terminal carboxyl groups of each of two peptide monomers. In another example, linkers containing two carboxyl groups, either preactivated or in the presence of a suitable coupling reagent, may be reacted with the N-terminal or side chain amine groups, or C-terminal lysine amides, of each of two peptide monomers.

Disulfide Bonds.

Generally, although not necessarily, peptide dimers will also contain one or more intramolecular disulfide bonds between cysteine residues of the peptide monomers. Preferably, the two monomers contain at least one intramolecular disulfide bond. Most preferably, both monomers of a peptide dimer contain an intramolecular disulfide bond, such that each monomer contains a cyclic group. Such disulfide bonds may be formed by oxidation of the cysteine residues of the peptide core sequence. In one embodiment the control of cysteine bond formation is exercised by choosing an oxidizing agent of the type and concentration effective to optimize formation of the desired isomer. For example, oxidation of a peptide dimer to form two intramolecular disulfide bonds (one on each peptide chain) is preferentially achieved (over formation of intermolecular disulfide bonds) when the oxidizing agent is DMSO. The formation of cysteine bonds can be controlled by the selective use of thiol-protecting groups during peptide synthesis.

Other embodiments of this invention provide for analogues of these disulfide derivatives in which one of the sulfurs has been replaced by a $CH_2$ group or other isotere for sulfur. These analogues can be prepared from the compounds of the present invention, wherein each core sequence contains at least one C or homocysteine residue and an α-amino-γ-butyric acid in place of the second C residue, via an intramolecular or intermolecular displacement, using methods known in the art (see, e.g., Barker, et al. (1992) J. Med. Chem. 35:2040-2048 and Or, et al. (1991) J. Org. Chem. 56:3146-3149). One of skill in the art will readily appreciate that this displacement can also occur using other homologs of α-amino-γ-butyric acid and homocysteine.

In addition to the foregoing cyclization strategies, other non-disulfide peptide cyclization strategies can be employed. Such alternative cyclization strategies include, for example, amide-cyclization strategies as well as those involving the formation of thio-ether bonds. Thus, the compounds of the present invention can exist in a cyclized form with either an intramolecular amide bond or an intramolecular thio-ether bond. For example, a peptide may be synthesized wherein one cysteine of the core sequence is replaced with lysine and the second cysteine is replaced with glutamic acid. Thereafter a cyclic monomer may be formed through an amide bond between the side chains of these two residues. Alternatively, a peptide may be synthesized wherein one cysteine of the core sequence is replaced with lysine. A cyclic monomer may then be formed through a thio-ether linkage between the side chains of the lysine residue and the second cysteine residue of the core sequence. As such, in addition to disulfide cyclization strategies, amide-cyclization strategies and thio-ether cyclization strategies can both be readily used to cyclize the compounds of the present invention. Alternatively, the amino-terminus of the peptide can be capped with an α-substituted acetic acid, wherein the α-substituent is a leaving group, such as an α-haloacetic acid, for example, α-chloroacetic acid, α-bromoacetic acid, or α-iodoacetic acid.

Spacers.

A peptide monomer or dimer may further comprise one or more spacer moieties. Such spacer moieties may be attached to a peptide monomer or to a peptide dimer (e.g., such spacer moieties may be attached to the linker $L_K$ moiety that connects the monomers of a peptide dimer). For example, such spacer moieties may be attached to a peptide via the carbonyl carbon of a lysine linker, or via the nitrogen atom of an iminodiacetic acid linker. Such a spacer may connect a peptide to an attached water soluble polymer moiety or a protecting group.

In one embodiment, the spacer moiety is a $C_{1-12}$ linking moiety optionally terminated with —NH— linkages or carboxyl (—COOH) groups, and optionally substituted at one or more available carbon atoms with a lower alkyl substituent. In one embodiment, the spacer is R—COOH wherein R is a lower ($C_{1-6}$) alkylene optionally substituted with a functional group such as a carboxyl group or an amino group that enables binding to another molecular moiety. For example, the spacer may be a glycine (G) residue, or an amino hexanoic acid.

In other embodiments, the spacer is —NH—R—NH— wherein R is a lower ($C_{1-6}$) alkylene substituted with a functional group such as a carboxyl group or an amino group that enables binding to another molecular moiety. For example, the spacer may be a lysine (K) residue or a lysine amide (K—$NH_2$, a lysine residue wherein the carboxyl group has been converted to an amide moiety —$CONH_2$).

A spacer can be incorporated into the peptide during peptide synthesis. For example, where a spacer contains a free amino group and a second functional group (e.g., a carboxyl group or an amino group) that enables binding to another molecular moiety, the spacer may be conjugated to the solid support. Thereafter, the peptide may be synthesized directly onto the spacer's free amino group by standard solid phase techniques.

For example, a spacer containing two functional groups is first coupled to the solid support via a first functional group. Next a linker $L_K$ moiety having two functional groups capable of serving as initiation sites for peptide synthesis and a third functional group (e.g., a carboxyl group or an amino group) that enables binding to another molecular moiety is conjugated to the spacer via the spacer's second functional group and the linker's third functional group. Thereafter, two peptide monomers may be synthesized directly onto the two reactive nitrogen groups of the linker $L_K$ moiety in a variation of the solid phase synthesis technique. For example, a solid support coupled spacer with a free amine group may be reacted with a lysine linker via the linker's free carboxyl group.

In alternate embodiments where the peptide compounds contain a spacer moiety, said spacer may be conjugated to the peptide after peptide synthesis. Such conjugation may be achieved by methods well established in the art. In one embodiment, the linker contains at least one functional group suitable for attachment to the target functional group of the synthesized peptide. For example, a spacer with a free amine group may be reacted with a peptide's C-terminal carboxyl group. In another example, a linker with a free carboxyl group may be reacted with the free amine group of a peptide's N-terminus or of a lysine residue. In yet another example, a spacer containing a free sulfhydryl group may be conjugated to a cysteine residue of a peptide by oxidation to form a disulfide bond.

Water Soluble Polymer Moieties.

The peptide monomers, dimers, or multimers of the invention may further comprise one or more water soluble polymer moieties. Preferably, these polymers are covalently attached to the peptide compounds of the invention. Included with the below description, the U.S. patent application Ser. No. 10/844,933 and International Patent Application No. PCT/US04/14887, filed May 12, 2004, are incorporated by reference herein in their entirety.

In recent years, water-soluble polymers, such as polyethylene glycol (PEG), have been used for the covalent modification of peptides of therapeutic and diagnostic importance. Attachment of such polymers is thought to enhance biological activity, prolong blood circulation time, reduce immunogenicity, increase aqueous solubility, and enhance resistance to protease digestion (see, e.g., J. M. Harris, Ed., "Biomedical and Biotechnical Applications of Polyethylene Glycol Chemistry," Plenum, New York, 1992; Knauf, et al. (1988) J. Biol. Chem. 263; 15064; Tsutsumi, et al. (1995) J. Controlled Release 33:447; Kita, et al. (1990) Drug Des. Delivery 6:157; Abuchowski, et al. (1977) J. Biol. Chem. 252:582; Beauchamp, et al. (1983) Anal. Biochem. 131:25; Chen, et al. (1981) Biochim. Biophy. Acta 660:293).

The water soluble polymers useful for the peptide compounds of the invention may be, for example, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl pyrrolidone)polyethylene glycol, propropylene glycol homopolymers, polypropylene oxide/ethylene oxide copolymers, and polyoxyethylated polyols.

The water soluble polymer may be of any molecular weight, and may be branched or unbranched. A preferred PEG for use in the present invention comprises linear, unbranched PEG having a low molecular weight. It is understood that in a given preparation of PEG, the molecular weights will typically vary among individual molecules. Some molecules will weight more, and some less, than the stated molecular weight. Such variation is generally reflect by use of the word "about" to describe molecular weights of the PEG molecules.

Peptides, peptide dimers and other peptide-based molecules of the invention can be attached to water-soluble polymers (e.g., PEG) using any of a variety of chemistries to link the water-soluble polymer(s) to the receptor-binding portion of the molecule (e.g., peptide+spacer). A typical embodiment employs a single attachment junction for covalent attachment of the water soluble polymer(s) to the receptor-binding portion, however in alternative embodiments multiple attachment junctions may be used, including further variations wherein different species of water-soluble polymer are attached to the receptor-binding portion at distinct attachment junctions, which may include covalent attachment junction(s) to the spacer and/or to one or both peptide chains. In some embodiments, the dimer or higher order multimer will comprise distinct species of peptide chain (i.e., a heterodimer or other heteromultimer). By way of example and not limitation, a dimer may comprise a first peptide chain having a PEG attachment junction and the second peptide chain may either lack a PEG attachment junction or utilize a different linkage chemistry than the first peptide chain and in some variations the spacer may contain or lack a PEG attachment junction and said spacer, if PEGylated, may utilize a linkage chemistry different than that of the first and/or second peptide chains. An alternative embodiment employs a PEG attached to the spacer portion of the receptor-binding portion and a different water-soluble polymer (e.g., a carbohydrate) conjugated to a side chain of one of the amino acids of the peptide portion of the molecule.

A wide variety of polyethylene glycol (PEG) species may be used for PEGylation of the receptor-binding portion (peptides+spacer). Substantially any suitable reactive PEG reagent can be used. In preferred embodiments, the reactive PEG reagent will result in formation of a carbamate or amide bond upon conjugation to the receptor-binding portion. Suitable reactive PEG species include, but are not limited to, those which are available for sale in the Drug Delivery Systems catalog (2003) of NOF Corporation (Yebisu Garden Place Tower, 20-3 Ebisu 4-chome, Shibuya-ku, Tokyo 150-6019) and the Molecular Engineering catalog (2003) of Nektar Therapeutics (490 Discovery Drive, Huntsville, Ala. 35806). For example and not limitation, the following PEG reagents are often preferred in various embodiments: mPEG2-NHS, mPEG2-ALD, multi-Arm PEG, mPEG(MAL)2, mPEG2(MAL), mPEG-NH2, mPEG-SPA, mPEG-SBA, mPEG-thioesters, mPEG-Double Esters, mPEG-BTC, mPEG-ButyrALD, mPEG-ACET, heterofunctional PEGs (NH2-PEG-COOH, Boc-PEG-NHS, Fmoc-PEG-NHS, NHS-PEG-VS, NHS-PEG-MAL), PEG acrylates (ACRL-PEG-NHS), PEG-phospholipids (e.g., mPEG-DSPE), multiarmed PEGs of the SUNBRITE series including the GL series of glycerine-based PEGs activated by a chemistry chosen by those skilled in the art, any of the SUNBRITE activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOH, hydroxyl-PEG-aldehyde, carboxylic anhydride type-PEG, functionalized PEG-phospholipid, and other similar and/or suitable reactive PEGs as selected by those skilled in the art for their particular application and usage.

The number of polymer molecules attached may vary; for example, one, two, three, or more water soluble polymers may be attached to a peptide of the invention. The multiple attached polymers may be the same or different chemical moieties (e.g., PEGs of different molecular weight). In some cases, the degree of polymer attachment (the number of polymer moieties attached to a peptide and/or the total number of peptides to which a polymer is attached) may be influenced by the proportion of polymer molecules versus peptide molecules in an attachment reaction, as well as by the total concentration of each in the reaction mixture. In general, the optimum polymer versus peptide ratio (in terms of reaction efficiency to provide for no excess unreacted peptides and/or polymer moieties) will be determined by factors such as the desired degree of polymer attachment (e.g., mono, di-, tri-, etc.), the molecular weight of the polymer selected, whether the polymer is branched or unbranched, and the reaction conditions for a particular attachment method.

There are a number of PEG attachment methods available to those skilled in the art (see, e.g., Goodson, et al. (1990) Bio/Technology 8:343; EP 0 401 384; Malik, et al., (1992) Exp. Hematol. 20:1028-1035; PCT Pub. No. WO 90/12874; U.S. Pat. No. 5,757,078; and U.S. Pat. No. 6,077,939). For example, activated PEG may be covalently bound to amino acid residues via a reactive group, such as a free amino group in N-terminal amino acid residues and lysine (K) residues or a free carboxyl group in C-terminal amino acid residues. Sulfhydryl groups (e.g., as found on cysteine residues) may also be used as a reactive group for attaching PEG. In addition, enzyme-assisted methods for introducing activated groups (e.g., hydrazide, aldehyde, and aromatic-amino groups) specifically at the C-terminus of a polypeptide have been described (Schwarz, et al. (1990) Methods Enzymol. 184:160; Rose, et al. (1991) Bioconjugate Chem. 2:154; Gaertner, et al. (1994) J. Biol. Chem. 269:7224).

For example, PEG molecules may be attached to peptide amino groups using methoxylated PEG ("mPEG") having different reactive moieties. Such polymers include mPEG-succinimidyl succinate, mPEG-succinimidyl carbonate, mPEG-imidate, mPEG-4-nitrophenyl carbonate, and mPEG-cyanuric chloride. Similarly, PEG molecules may be attached to peptide carboxyl groups using methoxylated PEG with a free amine group (mPEG-NH$_2$).

Where attachment of the PEG is non-specific and a peptide containing a specific PEG attachment is desired, the desired PEGylated compound may be purified from the mixture of PEGylated compounds. For example, if an N-terminally PEGylated peptide is desired, the N-terminally PEGylated form may be purified from a population of randomly PEGylated peptides (i.e., separating this moiety from other monoPEGylated moieties).

Site-specific PEGylation at the N-terminus, side chain, and C-terminus can be performed through (i) solid-phase synthesis (see, e.g., Felix, et al. (1995) Int. J. Peptide Protein Res. 46:253) or (ii) attaching a peptide to extremities of liposomal surface-grafted PEG chains in a site-specific manner through a reactive aldehyde group at the N-terminus generated by sodium periodate oxidation of N-terminal threonine (see, e.g., Zalipsky, et al. (1995) Bioconj. Chem. 6:705; this method is limited to polypeptides with N-terminal serine or threonine residues), or (iii) via a hydrazone, reduced hydrazone, oxime, or reduced oxime bond is described in U.S. Pat. No. 6,077,939.

In one method, selective N-terminal PEGylation may be accomplished by reductive alkylation which exploits differential reactivity of different types of primary amino groups (lysine versus the N-terminal) available for derivatization in a particular protein. Under the appropriate reaction conditions, a carbonyl group containing PEG is selective attached to the N-terminus of a peptide. For example, one may selectively N-terminally PEGylate the protein by performing the reaction at a pH which exploits the pK$_a$ differences between the ε-amino groups of a lysine residue and the α-amino group of the N-terminal residue of the peptide. By such selective attachment, PEGylation takes place predominantly at the N-terminus of the protein, with no significant modification of other reactive groups (e.g., lysine side chain amino groups). Using reductive alkylation, the PEG should have a single reactive aldehyde for coupling to the protein (e.g., PEG proprionaldehyde may be used).

Site-specific mutagenesis is a further approach which may be used to prepare peptides for site-specific polymer attachment. By this method, the amino acid sequence of a peptide is designed to incorporate an appropriate reactive group at the desired position within the peptide. For example, WO 90/12874 describes the site-directed PEGylation of proteins modified by the insertion of cysteine residues or the substitution of other residues for cysteine residues.

Where PEG is attached to a spacer or linker moiety, similar attachment methods may be used. In this case, the linker or spacer contains a reactive group and an activated PEG molecule containing the appropriate complementary reactive group is used to effect covalent attachment. In preferred embodiments the linker or spacer reactive group contains a terminal amino group (i.e., positioned at the terminus of the linker or spacer) which is reacted with a suitably activated PEG molecule to make a stable covalent bond such as an amide or a carbamate. Suitable activated PEG species include, but are not limited to, mPEG-para-nitrophenylcarbonate (mPEG-NPC), mPEG-succinimidyl carbonate (mPEG-SC), and mPEG-succinimidyl propionate (mPEG-SPA). In other preferred embodiments, the linker or spacer reactive group contains a carboxyl group capable of being activated to form a covalent bond with an amine-containing PEG molecule under suitable reaction conditions. Suitable PEG molecules include mPEG-NH$_2$ and suitable reaction conditions include carbodiimide-mediated amide formation or the like.

Preparation of the Peptides of the Invention

The peptides of the invention may be prepared by classical methods known in the art. These standard methods include exclusive solid phase synthesis, automated solid phase synthesis, partial solid phase synthesis methods, fragment condensation, classical solution synthesis, and recombinant DNA technology (See, e.g., Merrifield J. Am. Chem. Soc. 1963 85:2149 and Merrifield et al., 1982, Biochemistry, 21:502).

A preferred method for peptide synthesis is solid phase synthesis. Solid phase peptide synthesis procedures are well-known in the art (see, e.g., Stewart, *Solid Phase Peptide Syntheses*, Freeman and Co.: San Francisco, 1969; 2002/2003 General Catalog from Novabiochem Corp, San Diego, USA; Goodman, *Synthesis of Peptides and Peptidomimetics*, Houben-Weyl, Stuttgart 2002). In solid phase synthesis, synthesis is typically commenced from the C-terminal end of the peptide using an α-amino protected resin. A suitable starting material can be prepared, for instance, by attaching the required α-amino acid to a chloromethylated resin, a hydroxymethyl resin, a polystyrene resin, a benzhydrylamine resin, or the like. One such chloromethylated resin is sold under the trade name BIO-BEADS SX-1 by Bio Rad Laboratories (Richmond, Calif.). The preparation of the hydroxymethyl resin has been described (Bodonszky, et al. (1966) Chem. Ind. London 38:1597). The benzhydrylamine (BHA) resin has been described (Pietta and Marshall, 1970, Chem. Commun., 650), and the hydrochloride form is commercially available from Beckman Instruments, Inc. (Palo Alto, Calif.). For example, an α-amino protected amino acid may be coupled to a chloromethylated resin with the aid of a cesium bicarbonate catalyst, according to the method described by Gisin (1973, Helv. Chim. Acta 56:1467).

After initial coupling, the α-amino protecting group is removed, for example, using trifluoroacetic acid (TFA) or hydrochloric acid (HCl) solutions in organic solvents at room temperature. Thereafter, α-amino protected amino acids are successively coupled to a growing support-bound peptide chain. The α-amino protecting groups are those known to be useful in the art of stepwise synthesis of peptides, including: acyl-type protecting groups (e.g., formyl, trifluoroacetyl, acetyl), aromatic urethane-type protecting groups [e.g., benzyloxycarboyl (Cbz) and substituted Cbz], aliphatic urethane protecting groups [e.g., t-butyloxycarbonyl (Boc), isopropyloxycarbonyl, cyclohexyloxycarbonyl], and alkyl type protecting groups (e.g., benzyl, triphenylmethyl), fluorenylmethyl oxycarbonyl (Fmoc), allyloxycarbonyl (Alloc), and 1-(4,4-dimethyl-2,6-dioxocyclohex-1-ylidene)ethyl (Dde).

The side chain protecting groups (typically ethers, esters, trityl, PMC (2,2,5,7,8-pentamethyl-chroman-6-sulphonyl), and the like) remain intact during coupling and is not split off during the deprotection of the amino-terminus protecting group or during coupling. The side chain protecting group must be removable upon the completion of the synthesis of the final peptide and under reaction conditions that will not alter the target peptide. The side chain protecting groups for Tyr include tetrahydropyranyl, tert-butyl, trityl, benzyl, Cbz, Z—Br—Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting groups for Arg include nitro, Tosyl (Tos), Cbz, adamantyloxycarbonyl mesitoylsulfonyl (Mts), 2,2,4,6,7-pentamethyldihydrobenzofurane-5-sulfonyl (Pbf), 4-mthoxy-2,3,6-trimethyl-benzenesulfonyl (Mtr), or Boc. The side chain protecting groups for Lys include Cbz, 2-chlorobenzyloxycarbonyl (2-Cl-Cbz), 2-bromobenzyloxycarbonyl (2-Br—Cbz), Tos, or Boc.

After removal of the α-amino protecting group, the remaining protected amino acids are coupled stepwise in the desired order. Each protected amino acid is generally reacted in about a 3-fold excess using an appropriate carboxyl group activator such as 2-(1H-benzotriazol-1-yl)-1,1,3,3 tetramethyluronium hexafluorophosphate (HBTU) or dicyclohexylcarbodiimide (DCC) in solution, for example, in methylene chloride ($CH_2Cl_2$), N-methylpyrrolidone, dimethyl formamide (DMF), or mixtures thereof.

After the desired amino acid sequence has been completed, the desired peptide is decoupled from the resin support by treatment with a reagent, such as trifluoroacetic acid (TFA) or hydrogen fluoride (HF), which not only cleaves the peptide from the resin, but also cleaves all remaining side chain protecting groups. When a chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides. In preparing the esters of the invention, the resins used to prepare the peptide acids are employed, and the side chain protected peptide is cleaved with base and the appropriate alcohol (e.g., methanol). Side chain protecting groups are then removed in the usual fashion by treatment with hydrogen fluoride to obtain the desired ester. The resultant peptide can be further purified using HPLC.

These procedures can also be used to synthesize peptides in which amino acids other than the 20 naturally occurring, genetically encoded amino acids are substituted at one, two, or more positions of any of the compounds of the invention. Synthetic amino acids that can be substituted into the peptides of the present invention include, but are not limited to, N-methyl, L-hydroxypropyl, L-3,4-dihydroxyphenylalanyl, δ amino acids such as L-δ-hydroxylysyl and D-δ-methylalanyl, L-δ-methylalanyl, β amino acids, and isoquinolyl. D-amino acids and non-naturally occurring synthetic amino acids can also be incorporated into the peptides of the present invention.

In addition to chemical synthesis, the peptides of the present invention may be synthesized by employing recombinant DNA technology by expressing one or more polynucleotide comprising a peptide coding region. Thus, provided herein are isolated polynucleotides that encode the peptides of the present invention as well as recombinant vectors and host cells (both eukaryotic and prokaryotic) that have been genetically modified to express or overexpress the peptides of the present invention.

In one embodiment, the invention provides isolated polynucleotides comprising nucleotide sequences encoding the CEFH peptide of SEQ ID NO: 1. In another embodiment, the invention provides isolated polynucleotides comprising nucleotide sequences encoding the CEHH peptide of SEQ ID NO: 2.

Expression may be achieved in any conventional expression system known in the art by isolating a DNA fragment encoding the peptide of interest and cloning into an expression vector.

Other Compounds of the Invention

Useful compounds of the present invention are not limited to peptides incorporating natural and/or non-natural amino acids. A number of non-peptide molecules having similar functional properties can be developed to incorporate disparate chemical functional groups within a single molecule. These molecules are often referred to as scaffolding molecules, or scaffolds, since they can accommodate a wide range of chemical functionality and can be designed to present the chemical functional groups in a wide array of relative geometric orientations in space. Molecular scaffold systems include, but are not limited to, carbohydrates (see, e.g., Tamaruya et al., Angew Chem. Int. Ed. Engl., 2004, 43(21):2834-7), peptide nucleic acids (PNA's), (see, e.g., Peptide Nucleic Acids: Protocols and Applications, 2nd ed., Peter E. Nielsen, ed., Horizon Bioscience, 2004) and molecules not derived from biological precursors (see, e.g., Savinov and Austin, Org. Lett., 2002, 4(9):1419-22).

Chemical functionality comprising these molecules as well as peptides of the invention would include (i) at least one thiol group (for example, cysteine or homocysteine), (ii) at least one polar group (for example, a functional group with a measurable dipole moment, including, but not limited to, carbonyl groups such as in ketones, esters, or amides, imine groups alone or in heterocycles, cyano groups, guanidine groups, amidine groups, etc. as in serine, threonine, lysine, arginine, histidine, tyrosine, tryptophan, glutamic acid, aspartic acid, glutamine or asparagine, cysteine or methionine), (iii) at least one proton donor (such as an alcohol, carboxylic acid, hydroxylamine, heterocyclic or heteroaromatic NH or OH as in serine, threonine, lysine, arginine, histidine, tyrosine, tryptophan, glutamic acid, aspartic acid, glutamine or asparagine), and (iv) at least one aromatic group (for example, carbocyclic or heteroaromatic groups as in tyrosine, tryptophan, histidine or phenylalanine). It is envisioned that these chemical groups may be combined into a single functional group (for example tyrosine, tryptophan, histidine, glutamic acid, aspartic acid, glutamine, asparagine, arginine, and lysine) or be comprised in different portions of the molecule.

The incorporation of this diverse a set of chemistries may require chemical protection of reactive functionality during synthesis. These techniques are well known in the art and can be found in references such as T. W. Green, P. G. M. Wuts, Protective Groups in Organic Synthesis, Wiley-Interscience, New York, 1999.

Compositions Comprising One or More Compound(s) of the Invention

Tyrosine denitrating compounds disclosed herein may be formulated as compositions together with a pharmaceutically acceptable carrier (such as an adjuvant or vehicle) and/or excipient, and/or diluent A composition of this invention may include pharmaceutically acceptable salts of the components therein. Pharmaceutically acceptable salts include the acid addition salts (formed with the free amino groups of the peptide) that are formed with inorganic acids such as, for example, hydrochloric or phosphoric acids, or such organic acids as acetic, tartaric, mandelic and the like. Salts formed with the free carboxyl groups can be derived from inorganic bases such as, for example, sodium, potassium, ammonium, calcium or ferric hydroxides, and such organic bases as isopropylamine, trimethylamine, 2-ethylamino ethanol, histidine, procaine and the like.

Pharmaceutically acceptable carriers are familiar to those skilled in the art and can include sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E.W. Martin. For compositions formulated as liquid solutions, acceptable carriers and diluents include saline and sterile water, and may optionally include antioxidants, buffers, bacteriostats, and other common additives. The compositions can also be formulated as pills, capsules, granules, or tablets which may contain, in addition to a peptide of this invention, diluents, dispersing and surface active agents, binders, and lubricants. Proper formulation is dependent upon the route of administration chosen.

Methods for Identifying Additional Peptides Suitable for the Treatment of Diseases Associated with the Accumulation of 3-Nitrotyrosine The present invention also provides methods for generating and/or identifying novel peptides having the same or better functional characteristics as the CEFH peptides of the invention using the following design methods (aimed at preserving or improving the unique combination of stacking and/or ionic and/or hydrophobic interactions that allow the CEFH peptides to efficiently transfer the $NO_2$ group from the protein tyrosine to its thiol group):

(1) Combinatorial shuffling of the relative positions of CEFH amino acids to attain spatial arrangements of the catalysis components that are more active.

(2) Addition of a linker (e.g., homocysteine) instead of cysteine (*CEFH) to provide additional spatial flexibility and increase the reach of SH group as an acceptor of NO. This modification may also increase the overall hydrophobicity of the peptide and thus render it more cell- and protein globule-permeable.

(3) Introduction of electropositive substitutions (e.g., $CH_3$, $C_2H_5$, tret-Butyl, etc.) into the benzene ring of phenylalanine (CEF*H) to increase the stacking interaction between protein 3-NT and phenylalanine. This modification also increases the overall hydrophobicity of the peptide and thus renders it more cell- and protein globule-permeable.

(4) Introduction of tryptophan or cyclic aromatic groups (both natural and synthetic, e.g., naphtalene, tyrosine, and histidine) instead of phenylalanine (CE[F→AR*]H) to stabilize the stacking interaction with protein 3-NT because of two conjugated aromatic rings.

(5) Substitution of phenylalanine with one or more histidines (CE[F→H]H) with or without an electropositive substitution (e.g., $CH_3$, $C_2H_5$, tret-Butyl, etc.) to increase the efficiency of denitration of the tyrosine of the protein;

(6) Modification that increases pKa of glutamic acid (e.g., OH, $NO_2$, or halide in alpha-position) (CE*FH) to increase of the rate of denitration.

(7) Substitution of glutamic acid with aspartic acid with or without modifications that increase its pKa (e.g., OH, $NO_2$, or halide in alpha-position) (C[E→D]FH (SEQ ID NO: 14) or C[E→D*]FH);

The present invention further provides in vitro and in vivo methods for functional testing of the novel denitrating peptides generated using the above methods, comprising:

(1) in vitro testing by adding the peptide to a nitrated protein having 3-NT (e.g., ONOO-nitrated albumin) and monitoring the disappearance of 3-NT (e.g., by immunoblotting using anti-3-NT antibodies);

(2) testing by adding the peptide to a cell culture treated with NO and/or reactive NO species (e.g., subject to NO/ONOO-exposure) and measuring cell survival by methods such as an MTS-based assay (using the MTS reagent available from Promega) or the direct counting of apoptotic cells using flow cytometry.

(3) testing by adding the peptide to a cell culture treated with NO and/or reactive NO species (e.g., subject to NO/ONOO-exposure) and measuring the disappearance of 3-NT;

(4) in vivo testing by administering the peptide to an animal model of a relevant disease (e.g., I/R injury, septic shock, Alzheimer's disease, etc.) and monitoring disease progression;

(5) in vivo testing by administering the peptide to an animal model for I/R injury and determining the size of the infarct using a p-nitro-blue tetrazolium (NBT)-based assay while also monitoring functional parameters such as heart rate, mean arterial blood pressure, cardiac output, etc. Identification of improved peptides of the invention can be conducted in a format of high-throughput screening (HTS) assays, including both cell-based and cell-free assays. See, e.g., Furka et al. (14th International Congress of Biochemistry, 1988, Volume #5, Abstract FR:013; Furka, Int. J. Peptide Protein Res. 1991; 37:487-493), U.S. Pat. Nos. 4,631,211 and 5,010,175.

Methods for the Use of the Compounds of the Invention and Compositions Thereof The compounds of the invention and compositions thereof are useful in a wide variety of therapeutic applications including, but not limited to, the treatment of tissue damage associated with NO and its reactive species. For example, the compounds and compositions of the present invention can be used to treat diseases including, but not limited to, tissue damage associated with I/R injury of various tissues (e.g., I/R injury of heart muscle associated with heart attack or cardiac surgery, I/R injury of brain tissue associated with stroke, I/R injury of liver tissue, skeletal muscles, etc.), septic shock, anaphylactic shock, neurodegenerative diseases (e.g., Alzheimer's and Parkinson's diseases), neuronal injury, atherosclerosis, diabetes, multiple sclerosis, autoimmune uveitis, pulmonary fibrosis, oobliterative bronchiolitis, bronchopulmonary dysplasia (BPD), amyotrophic lateral sclerosis (ALS), sepsis, inflammatory bowel disease, arthritis, allograft rejection, autoimmune myocarditis, myocardial inflammation, pulmonary granulomatous inflammation, influenza- or HSV-induced pneumonia, chronic cerebral vasospasm, allergic encephalomyelitis, central nervous system (CNS) inflammation, *Heliobacterium pylori* gastritis, necrotizing entrerocolitis, celliac disease, peritonitis, early prosthesis failure, inclusion body myositis, preeclamptic pregnancies, skin lesions with anaphylactoid purpura, nephrosclerosis, ileitis, leishmaniasis, cancer, and related disorders.

Such methods include administering a composition of this invention to an animal/patient in an amount effective to treat tissue damage.

The optimal therapeutically effective amount of a compound or composition of this invention may be determined experimentally, taking into consideration the exact mode of administration, the form in which the drug is administered, the indication toward which the administration is directed, the subject involved (e.g., body weight, health, age, sex, etc.), and the preference and experience of the physician or veterinarian in charge.

As disclosed herein, the concentrations of CEFH peptides administered in the present invention are both therapeutically effective and pharmaceutically acceptable. The L-CEFH (SEQ ID NO: 1) peptide of the present invention is preferably used to treat or prevent tissue damage in vivo at 0.1-3.5 mg/kg, most preferably at 0.7 mg/kg. The D-CEFH peptide of the present invention is preferably used at 0.01-0.5 mg/kg, most preferably at 0.1 mg/kg.

The efficacy of the peptides and compositions of this invention can be determined using the in vitro and in vivo assays described in the Examples section, below.

Following methodologies which are well-established in the art, effective doses and toxicity of the peptides and compositions of the present invention, which performed well in in vitro tests, can be determined in studies using small animal models (e.g., mice, rats or dogs) in which they have been found to be therapeutically effective and in which these drugs can be administered by the same route proposed for the human trials.

For any pharmaceutical composition used in the methods of the invention, dose-response curves derived from animal systems can be used to determine testing doses for administration to humans. In safety determinations for each composition, the dose and frequency of administration should meet or exceed those anticipated for use in any clinical trial.

As disclosed herein, the dose of the compound in the compositions of the present invention is determined to ensure that the dose administered continuously or intermittently will not exceed an amount determined after consideration of the results in test animals and the individual conditions of a patient. A specific dose naturally varies (and is ultimately decided according to the judgment of the practitioner and each patient's circumstances) depending on the dosage procedure, the conditions of a patient or a subject animal such as age, body weight, sex, sensitivity, feed, dosage period, drugs used in combination, seriousness of the disease, etc.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$.

Delivery of the Peptides of the Invention to the Target Damaged Tissue

All known peptide delivery methods can be used to deliver the peptides of the present invention to the target damaged cells and tissues. The specific type of delivery useful for a given peptide is determined by its specific size, flexibility, conformation, biochemical properties of constituent amino acids, and amino acid arrangement. Peptide composition also determines, in part, the degree of protein binding, enzymatic stability, cellular sequestration, uptake into non-target tissue, clearance rate, and affinity for protein carriers. Other aspects independent of peptide composition must also be considered, such as cerebral blood flow, diet, age, sex, species (for experimental studies), dosing route, and effects of existing pathological conditions.

Examples of delivery methods useful for obtaining effective tissue delivery of the peptides of the invention (and effective passage through the blood-brain-barrier [BBB] in case of brain tissues), include, without limitation (reviewed, e.g., in Witt and Davis, AAPS Journal, 2006; 8(1): E76-E88.):

(i) invasive procedures (e.g., direct injection [e.g., using an external pump or i.v. line], transient osmotic opening, shunts, and biodegradable implants);

(ii) pharmacologically-based approaches to increase the tissue delivery by chemical modification of the peptide molecule itself, or by the attachment or encapsulation of the peptide in a substance that increases permeability, stability, bioavailability, and/or receptor affinity; in addition, modification of a peptide structure and/or addition of constituents (e.g., lipophilicity enhancers, polymers, antibodies) may enhance local peptide concentration in the target tissue;

(iii) physiologic-based strategies which exploit various carrier mechanisms; these strategies can be combined, dependent of the nature of a given peptide, creating "hybrid" peptides, resulting in synergistic delivery and end-effect.

Specific examples of peptide modifications and methods useful for improving delivery of the peptides of the invention include, without limitation, lipidization (e.g., methylation, dimethylation, or halogenation of constituent amino acids or acylation or alkylation of the N-terminal amino acid), structural modification to enhance stability (e.g., use of D-amino acids, N-acylation, or cyclization, e.g., via a disulfide-bridge or via a hydrazide bridge), glycosylation (e.g., adding simple sugars such as, e.g., glucose or xylose), increasing affinity for nutrient transporters (e.g., adding hexose or large neutral amino acid carriers which facilitate delivery of substrates to the brain), forming a prodrug by conjugating a peptide to a molecule with a known transporter activity or to a lipophilicity enhancer, which is cleaved at or near the site of action (e.g., using esterification [with, e.g., aromatic benzoyl esters or branched chain tertiary butyl esters] or amidation of amino, hydroxyl, or carboxylic acid-containing peptides; also, redox system-mediated delivery to the brain may be facilitated using conjugation to a methyldihydropyridine carrier and subsequent oxidation by NADH-linked dehydrogenases in the brain, which results in a quaternary ammonium salt, which does not cross back through the BBB endothelium), vector-based delivery (e.g., by coupling a peptide to a substance that increases the affinity to and transport across biological membranes via receptor-mediated or absorptive-mediated endocytosis followed by peptide release via enzymatic cleavage [e.g., conjugation of a peptide to murine monoclonal antibody (OX26) to the transferrin or conjugation to cationized albumin to increase brain uptake]), cationization to increase membrane entry via absorptive-mediated endocytosis, and polymer conjugation/encapsulation (e.g., conjugation to poly(ethylene glycol) [PEG] or poly(styrene maleic acid) or encapsulation via micro- or nano-particles [e.g., polymeric nanoparticles ranging in size between 10 and 1000 nm, which have a polysorbate overcoating such as, e.g., polysorbate-80], liposomes [e.g., surface-modified long-circulating liposomes grafted with a flexible hydrophilic polymer such as, e.g., PEG and/or liposomes composed of a phospholipid bilayer such as, e.g., pluronic copolymer P85, that act as a carrier for both hydrophilic and hydrophobic peptides], micelles [e.g., stable polymeric micelles prepared from amphiphilic PEG-phospholipid conjugates], or cell ghosts). Reviewed in Torchilin and Lukyanov, DDT, 2003, 8(6): 259-266; Egleton and Davis, NeuroRx, 2005, 2: 44-53; Witt and Davis, AAPS Journal, 2006; 8(1): E76-E88.

Regardless of the delivery method used, an important aspect of the present invention is to keep the size of the resulting delivered peptide sufficiently small (e.g., by using cleavable conjugates) to facilitate its access to various regions within the nitrated target protein.

Oral Delivery.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013, 556). A description of possible solid dosage forms for the therapeutic is given by Marshall, K. In: *Modern Pharmaceutics* Edited by G.S. Banker and C.T. Rhodes Chapter 10, 1979, herein incorporated by reference. In general, the formulation will include a peptide of the invention (or chemically modified forms thereof) and inert ingredients which allow for protection against the stomach environment, and release of the biologically active material in the intestine.

Also contemplated for use herein are liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

As discussed above, the peptides may be chemically modified so that oral delivery of the derivative is efficacious. Generally, the chemical modification contemplated is the attachment of at least one moiety to the component molecule itself, where said moiety permits (a) increase in peptide stability (e.g., by inhibition of proteolysis) and (b) efficient uptake into the blood stream from the stomach or intestine. As discussed above, common delivery-improving peptide modifications include PEGylation or the addition of moieties such as propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane (see, e.g., Abuchowski and Davis (1981) "Soluble Polymer-Enzyme Adducts," in *Enzymes as Drugs*. Hocenberg and Roberts, eds. (Wiley-Interscience: New York, N.Y.) pp. 367-383; and Newmark, et al. (1982) J. Appl. Biochem. 4:185-189).

For oral formulations, the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the peptide (or derivative) or by release of the peptide (or derivative) beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used.

The peptide (or derivative) can be included in the formulation as fine multiparticulates in the form of granules or pellets of particle size about 1 mm. The formulation of the material for capsule administration could also be as a powder, lightly compressed plugs, or even as tablets. These therapeutics could be prepared by compression.

Colorants and/or flavoring agents may also be included. For example, the peptide (or derivative) may be formulated (such as by liposome or microsphere encapsulation) and then further contained within an edible product, such as a refrigerated beverage containing colorants and flavoring agents.

One may dilute or increase the volume of the peptide (or derivative) with an inert material. These diluents could include carbohydrates, especially mannitol, lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress, and Avicel.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. The disintegrants may also be insoluble cationic exchange resins. Powdered gums may be used as disintegrants and as binders, and can include powdered gums such as agar, Karaya or tragacanth. Alginic acid and its sodium salt are also useful as disintegrants.

Binders may be used to hold the peptide (or derivative) agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An antifrictional agent may be included in the formulation of the peptide (or derivative) to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the peptide (or derivative) into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the peptide (or derivative) are for instance the fatty acids oleic acid, linoleic acid and linolenic acid.

Controlled release oral formulations may be desirable. The peptide (or derivative) could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The peptide (or derivative) could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols.

The second group consists of the enteric materials that are commonly esters of phthalic acid.

A mix of materials might be used to provide the optimum film coating. Film coating may be carried out in a pan coater or in a fluidized bed or by compression coating.

Parenteral Delivery.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Preferably, the L-peptides of the invention (e.g., L-CEFH; SEQ ID NO: 1) are administered to treat diseases related to NO damage by parental i.v. injection in a standard physiological solution. The D-peptides of the invention (e.g., D-CEFH) can be administered using any standard administration technique known in the art, such as oral administration.

The peptides can also be delivered using a vector (such as a viral vector) with the ability to express a peptide of this invention.

Combination Therapy

The novel anti-tissue damage peptides and compositions of the present invention can be used in conjunction with small thiols (such as, e.g., homocysteine, N-acetylcysteine (NAC), lipoic acid, thioredoxin (TRX), Bucillamine, etc., where a preferred small thiol is α-lipoic acid) as well as existing anti-inflammatory therapeutics such as inhibitors of TNF-α, inhibitors of COX-1/COX-2, inhibitors of IL-1β, etc. In a specific embodiment, the novel therapeutics of the invention are administered in combination with Non-Steroidal Anti-Inflammatory Drugs (NSAIDs). Suitable NSAIDs include, but are not limited to, those which inhibit cyclooxygenase, the enzyme responsible for the biosyntheses of the prostaglandins and certain autocoid inhibitors, including inhibitors of the various isoenzymes of cyclooxygenase (including, but not limited to, cyclooxygenase-1 and -2), and as inhibitors of both cyclooxygenase and lipoxygenase relates to NSAID, such as the commercially available NSAIDs aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celecoxib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acetyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine. Additional NSAID genera and particular NSAID compounds are disclosed in U.S. Pat. No. 6,297,260 and International Patent Application No. WO 01/87890.

EXAMPLES

The present invention will be better understood by reference to the following non-limiting examples.

Example 1

Identification of CEFH Peptide as Efficient Compound for Mediating Denitration of 3-Nitrotyrosine In Vitro The CEFH peptides were designed using the free docking software program, ArgusLab 4.0 (available on the World Wide Web at planaria-software.com/arguslab40.htm), to calculate the interaction energy between molecules. L-CEFH (SEQ ID NO: 1) peptide and D-CEFH peptide were synthesized and purified by New England Peptides Inc (Gardner, Mass.) and GL Biochem Ltd. (Shanghai), respectively, using a standard solid phase Fmoc protocol. D-CEFH was synthesized since this peptide is less prone to proteolysis compared to its L-CEFH counterpart. Peptides without His or Cys did not work.

Several groups have previously reported an in vivo denitration phenomenon (e.g., Kamisaki et al (1998) *Proc Natl Acad Sci USA* 95: 11584-11589; Aulak et al (2004) *Am J Physiol Heart Circ Physiol* 286: H30-H38). However, they tried to isolate denitration activity using pure 3-NT and failed. The present inventors have hypothesized that the stability of pure 3-NT is much higher than the stability of 3-NT incorporated in a protein and used ONOO-nitrated albumin as the substrate for detecting denitration activity.

Figure 2:
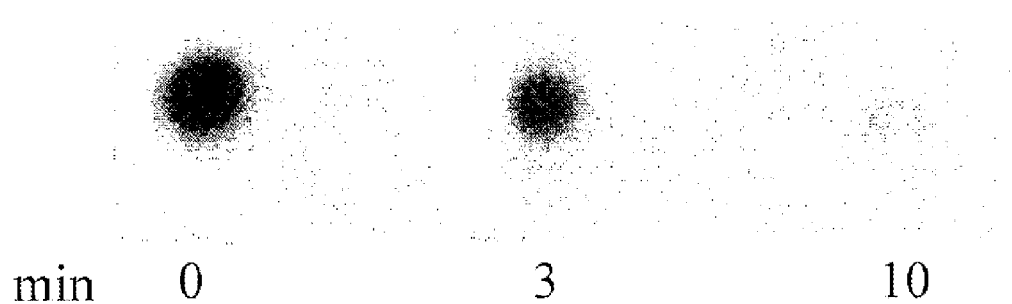
FIG. 2 is a dot-immunoblotting of a reaction mixture using antibodies against 3-NT showing the time course of L-CEFH (SEQ ID NO: 1) peptide-mediated denitration of peroxynitrite (ONOO)-nitrated albumin. Essentially complete denitration (>90%) was achieved after 10 minutes of treatment with 20 μM L-CEFH peptide solution containing 10 mM Tris HCl pH 7.2 at a temperature of 25° C.

To test the ability of L-CEFH peptide (Cys-Glu-Phe-His; SEQ ID NO: 1) to mediate 3-NT denitration in vitro, 20 µM CEFH peptide solution containing 10 mM Tris HCl pH 7.2 was added to albumin previously nitrated by peroxynitrite (ONOO⁻). Denitration of the peroxynitrite (ONOO)-nitrated albumin following 0, 3, or 10 minutes of incubation with L-CEFH peptide was then visualized by dot-immunoblotting with antibodies against 3-NT. As shown in FIG. 2, essentially complete denitration (i.e., >90%) was achieved after 10 minutes of treatment with 20 µM L-CEFC peptide solution containing 10 mM Tris HCl pH 7.2 at a temperature of 25° C.

Example 2

Figure 3:
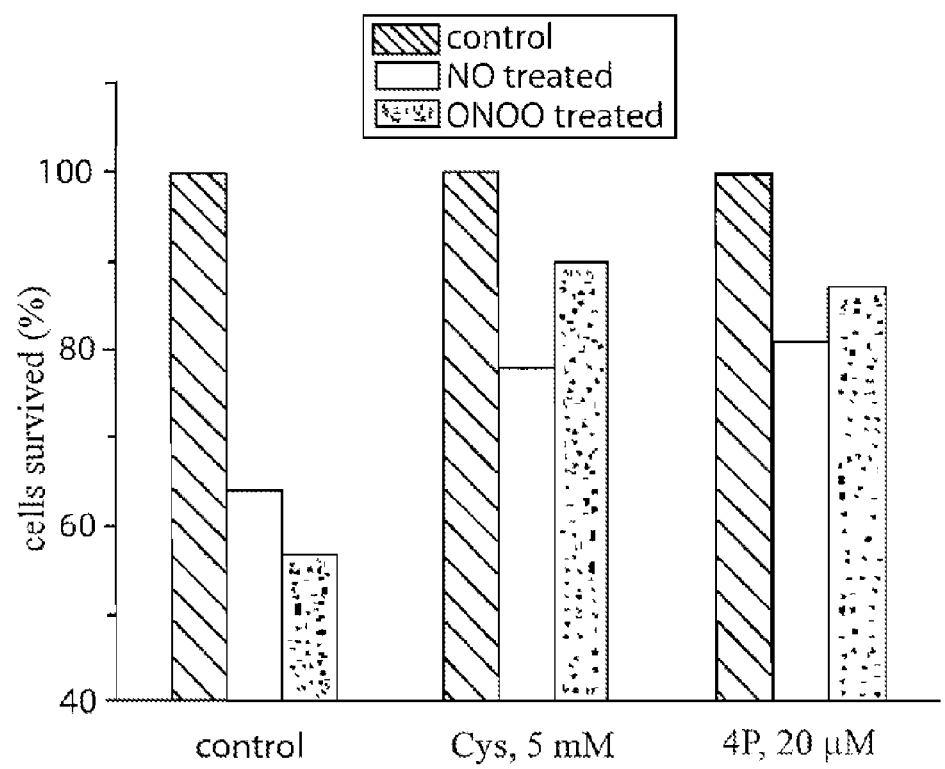
FIG. 3 is a bar graph showing that, as compared to "no treatment" control, both cysteine (Cys, at 5 mM) and L-CEFH (SEQ ID NO: 1) peptide (4P, at 20 μM) improve HeLa cell survival (by 60-80%) upon NO/ONOO-exposure, when added to HeLa cell culture for 40 minutes as measured by an MTS-based assay (available from Promega, Madison, Wis.). The L-CEFH peptide shows efficacy equivalent to cysteine, when used at 250 times lower concentration than cysteine.

CEFH Peptide Efficiently Reduces Cell Death Mediated by Nitric Oxide and Peroxynitrite The ability of the L-CEFH peptide (Cys-Glu-Phe-His; SEQ ID NO: 1) to reduce cell death caused by nitric oxide (NO) and peroxynitrite (ONOO⁻) was tested in cell culture. Following treatment with NO/ONOO⁻, HeLa cells were incubated with either a control buffer, 5 mM cysteine, or 20 µM L-CEFH peptide for 40 minutes. The percentage of cells surviving was determined by a MTS-based assay (available from Promega, Madison, Wis.). As shown in FIG. 3, as compared to "no treatment" control, both cysteine (Cys, at 5 mM) and L-CEFH peptide (4P, at 20 µM) improved HeLa cell survival to the same extent (i.e., by 60-80%). Importantly, the L-CEFH peptide showed the same efficacy as cysteine, when used at 250 times lower concentration.

Example 3

CEFH Peptide Reduces Myocardial Ischemia-Reperfusion Injury and 3-Nitrotyrosine Accumulation In Vivo The effect of the L-CEFH peptide (Cys-Glu-Phe-His; SEQ ID NO: 1) on the extent of myocardial ischemia-reperfusion (MI/R) injury and on the accumulation of 3-nitrotyrosine (3-NT) in myocardial tissue upon myocardial infarction was tested in a rat model in vivo.

Myocardial ischemia (MI) was produced in anaesthetized adult male Wistar rats (300-350 grams) under controlled ventilation. After thoracotomy at the fourth intercostal space, the heart was exteriorized and a 6-0 silk ligature was passed under the left coronary artery with a needle. After 30 minutes of MI, the ligature was released and the myocardium was reperfused for 1 hour. Rats were randomized 5 minutes after the beginning of reperfusion to receive either vehicle (control, n=6) or L-CEFH peptide (0.7 mg/kg; n=9) i.v. The extent of MI/R injury, or infarct size, was determined by calculating the ratio of the area of necrosis (NA) to the area at risk (AR). Accumulation of 3-NT in the tested heart tissue corresponding to the area at risk was analyzed by Western dot-immunoblotting of total protein (extracted from the area at risk) with antibodies against 3-NT.

Figure 4:
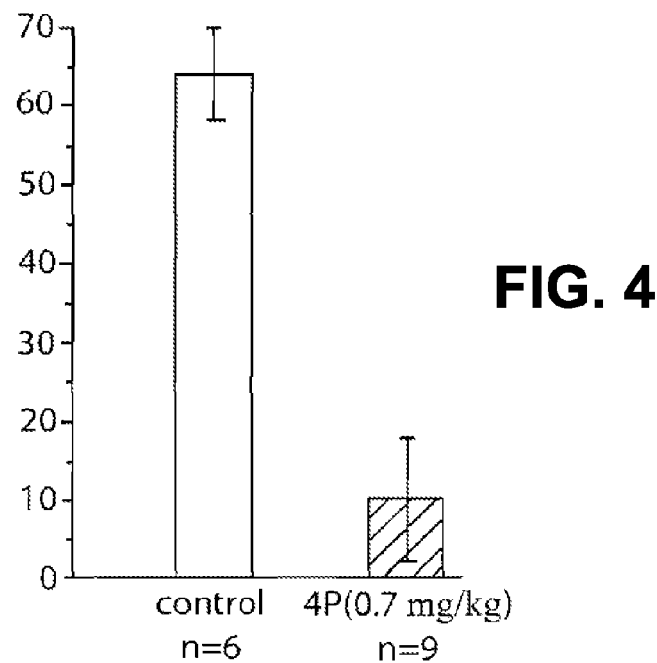
FIG. 4 is a bar graph showing that L-CEFH (SEQ ID NO: 1) peptide prevents myocardial ischemia-reperfusion (MI/R) injury in a rat model of myocardial infarction. Tested rats received either vehicle (control, n=6) or L-CEFH peptide (4P, 0.7 mg/kg; n=9) i.v. 5 minutes after beginning of reperfusion. Infarct size (necrotic area NA) is expressed as a percentage of the area at risk (AR). The decrease in the infarct size in the presence of the L-CEFH peptide is 3-5 fold as compared to the control.

As shown in FIG. 4, the L-CEFH peptide (4P) efficiently prevents MI/R injury in a rat model of myocardial infarction. The decrease in the infarct size in the presence of the L-CEFH peptide is 3-5 fold as compared to the control.

Figure 5:
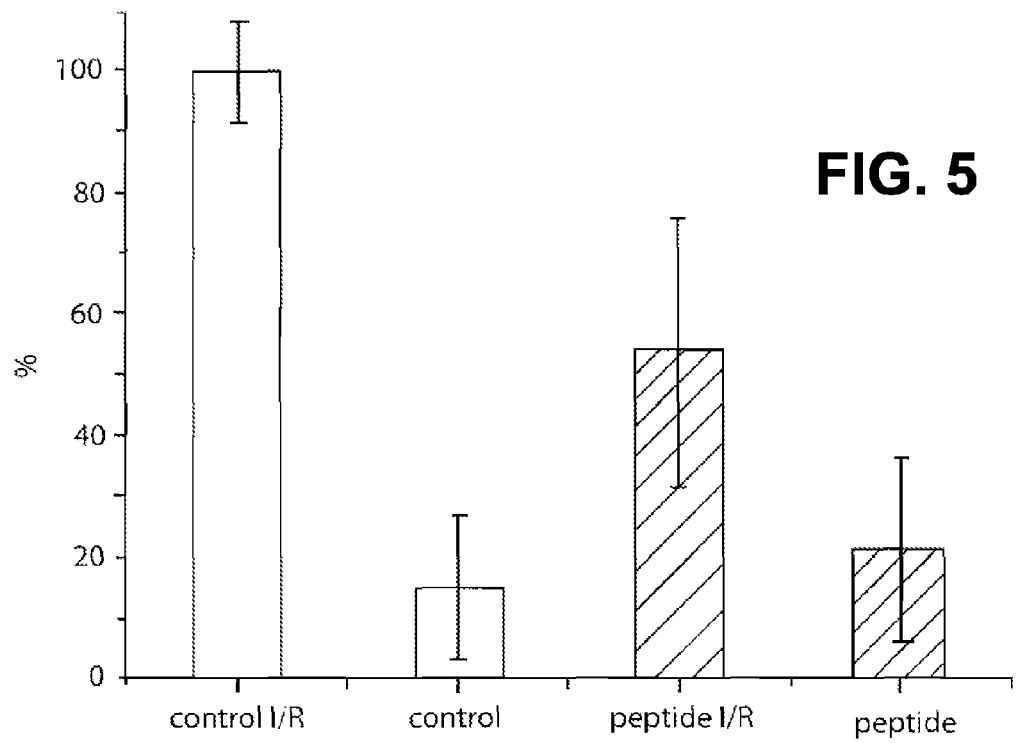
FIG. 5 is a bar graph showing that L-CEFH (SEQ ID NO: 1) peptide prevents accumulation of 3-NT in a rat model of MI. Hearts from the experiment in FIG. 4 were analyzed for the presence of 3-NT by dot-immunoblotting of the total protein from the heart tissue corresponding to the area at risk with anti-3-NT antibodies (see images under the graph). The vertical graph axis shows the percentage (%) of nitrated protein in control animals (no I/R) and peptide-treated I/R animals in relation to the non-treated I/R animals. As compared to the control, in the peptide-treated I/R animals, the 3-NT accumulation is reduced by about 70%.

As shown in FIG. 5, the L-CEFH peptide prevents accumulation of 3-NT in the heart tissue in a rat model of myocardial infarction. As compared to the control, in the peptide-treated I/R animals, the 3-NT accumulation is reduced by about 70%.

Example 4

D-CEFH Peptide has a Superior Activity in Reducing Myocardial Ischemia-Reperfusion Injury as Compared to L-CEFH To determine whether CEFH activity can be improved when replacing L-amino acids with D-amino acids, D-CEFH peptide consisting of all D-amino acids (Cys-Glu-Phe-His) was generated and its activity was compared to the activity of the original L-CEFH (SEQ ID NO: 1) peptide containing all L-amino acids in vivo in a rat model of myocardial infarction.

Rat model of myocardial infarction was generated as disclosed in Example 3, above. 0, 0.02, 0.05, 0.1, 0.14, 0.35, and 0.7 mg/kg of D-CEFH peptide (n4 for each concentration) were administered i.v. The extent of MI/R injury, or infarct size, was determined by calculating the ratio of the area of necrosis (NA) to the area at risk (AR).

Figure 6:
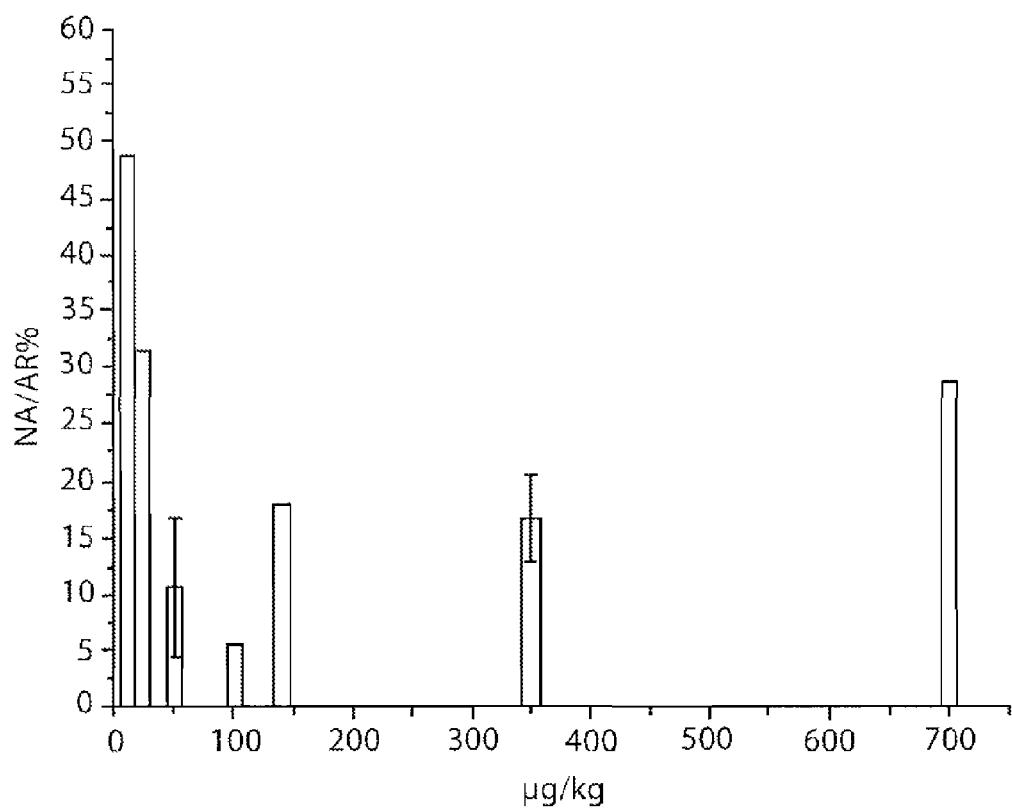
FIG. 6 is a bar graph showing that D-CEFH peptide has a superior activity in preventing MI/R injury as compared to L-CEFH (SEQ ID NO: 1) peptide in a rat model of MI. Under the same experimental conditions as in FIG. 4, different concentrations of D-CEFH peptide (0, 0.02, 0.05, 0.1, 0.14, 0.35, and 0.7 mg/kg; n≤4 for each concentration) were administered i.v. Infarct size (necrotic area NA) is expressed as a percentage of the area at risk (AR). While L-CEFH produces its maximal effect in preventing MI/R injury when used at 0.7 mg/kg, D-CEFH produces the same effect in preventing MI/R injury when used at 14-fold lower concentration, i.e., 0.05 mg/kg, and produces its maximal effect at 0.1 mg/kg.

As shown in FIG. 6, D-CEFH peptide has a superior activity in preventing MI/R injury as compared to L-CEFH peptide in a rat model of MI. While L-CEFH (SEQ ID NO: 1) produces its maximal effect in preventing MI/R injury when used at 0.7 mg/kg, the D-CEFH peptide produces the same effect in preventing MI/R injury when used at 14-fold lower concentration, i.e., 0.05 mg/kg, and produces its maximal effect at 0.1 mg/kg.

Example 5

Investigation of Long-Term Protective Effects of CEFH Peptide on Standard Heart Functional Parameters in a Rat Model of Myocardial Infarction Rat model of myocardial infarction is generated as disclosed in Example 3, above. ECG is performed to monitor the standard heart functional parameters 1, 2, 3, 4 weeks after I/R surgery.

Example 6

Protective Effects of CEFH Peptide in a Mouse Model of Anaphylactic Shock

Anaphylactic shock is a sudden, life-threatening allergic reaction associated with severe hypotension. Excessive production of the vasodilator NO contributes to this inflammatory hypotension and shock.

Mouse models of anaphylactic shock are created generally as outlined in Cauwels et al., J. Clin. Invest., 2006, 116(8): 2244-2251. Female C57BL/6 mice are housed in temperature-controlled, air-conditioned facilities with 14-hour light/10-hour dark cycles and food and water ad libitum. All data are collected using mice 8-12 weeks of age.

PAF-Induced Anaphylactic Shock Model.

Platelet-activating factor (PAF) is implicated in the cardiovascular dysfunctions occurring in various shock syndromes, including anaphylaxis. Intravenous PAF injection in conscious mice elicits rapid shock and results in death within 20-30 minutes. In the model, mice are injected intravenously with 55 μg PAF (1-O-alkyl-2-acetyl-sn-glycero-3-phosphocholine; Sigma-Aldrich). Mortality is scored up to 7 days after challenge. In experimental animals, 0.1 mg/kg D-CEFH peptide (Cys-Glu-Phe-His) is administered i.v. 1 hour before PAF.

BSA/OVA-Induced Anaphylactic Shock Model.

Mice are first sensitized with BSA or OVA in the presence of adjuvants. Two different sensitization models are used:

(a) Mice are given a single i.p. injection of 1 mg BSA (Sigma-Aldrich) mixed with 300 ng pertussis toxin (Sigma-Aldrich). Anaphylaxis is elicited 15 days later by i.v. injection of 2 mg of BSA.

(b) Mice are sensitized by i.p. injection of 100 μg OVA (Sigma-Aldrich), aluminum hydroxide (Sigma-Aldrich, 1 mg) and pertussis toxin (300 ng). Mice are challenged 19-20 days later by i.v. injection of 150 μg OVA.

Soon after challenge, mice develop severe hypothermia and rapidly succumb to systemic shock reaction. Mortality is scored up to 7 days after challenge. In experimental animals, the D-CEFH peptide is administered by i.v. injection 2 hours prior to challenge with a lethal dose of BSA or OVA.

What is claimed is:

1. A method for stimulating denitration of 3-nitrotyrosine in a cell or tissue of an animal, said method comprising administering to the cell or tissue a peptide which is between four amino acids and eight amino acids long and comprises the amino acid sequence $Xaa_1$-$Xaa_2$-$Xaa_3$-$Xaa_4$ (SEQ ID NO: 15), wherein $Xaa_1$ is L-Cys or D-Cys, $Xaa_2$ is L-Glu or D-Glu, $Xaa_3$ is L-Phe or D-Phe, and $Xaa_4$ is L-His or D-His, wherein in the peptide at least one amino acid is D-amino acid.

2. A method for reducing ischemia-reperfusion injury in a tissue of an animal, said method comprising administering to the tissue a peptide which is between four amino acids and eight amino acids long and comprises the amino acid sequence $Xaa_1$-$Xaa_2$-$Xaa_3$-$Xaa_4$ (SEQ ID NO: 15), wherein $Xaa_1$ is L-Cys or D-Cys, $Xaa_2$ is L-Glu or D-Glu, $Xaa_3$ is L-Phe or D-Phe, and $Xaa_4$ is L-His or D-His, wherein in the peptide at least one amino acid is D-amino acid.

3. The method of claim 1, wherein the peptide is a cyclic peptide.

4. The method of claim 1, wherein the peptide consists of the amino acid sequence Cys-Glu-Phe-His, wherein all amino acids in the peptide are D-amino acids.

5. The method of claim 1, wherein in the peptide all amino acids are D-amino acids.

6. The method of claim 2, wherein the peptide is a cyclic peptide.

7. The method of claim 2, wherein the peptide consists of the amino acid sequence Cys-Glu-Phe-His, wherein all amino acids in the peptide are D-amino acids.

8. The method of claim 2, wherein in the peptide all amino acids are D-amino acids.

* * * * *

SEQUENCE LISTING

```
<160> NUMBER OF SEQ ID NOS: 15

<210> SEQ ID NO 1
<211> LENGTH: 4
<212> TYPE: PRT
<213> ORGANISM: Artificial Sequence
<220> FEATURE:
<223> OTHER INFORMATION: synthetic peptide

<400> SEQUENCE: 1

Cys Glu Phe His
1

<210> SEQ ID NO 2
<211> LENGTH: 4
<212> TYPE: PRT
<213> ORGANISM: Artificial Sequence
<220> FEATURE:
<223> OTHER INFORMATION: synthetic peptide

<400> SEQUENCE: 2

Cys Glu His His
1

<210> SEQ ID NO 3
<211> LENGTH: 8
<212> TYPE: PRT
<213> ORGANISM: Artificial Sequence
<220> FEATURE:
<223> OTHER INFORMATION: synthetic peptide

<400> SEQUENCE: 3

Cys Glu Phe His Cys Glu Phe His
1               5
```

```
<210> SEQ ID NO 4
<211> LENGTH: 4
<212> TYPE: PRT
<213> ORGANISM: Artificial Sequence
<220> FEATURE:
<223> OTHER INFORMATION: synthetic peptide

<400> SEQUENCE: 4

His Cys Glu Phe
1

<210> SEQ ID NO 5
<211> LENGTH: 4
<212> TYPE: PRT
<213> ORGANISM: Artificial Sequence
<220> FEATURE:
<223> OTHER INFORMATION: synthetic peptide

<400> SEQUENCE: 5

Phe His Cys Glu
1

<210> SEQ ID NO 6
<211> LENGTH: 4
<212> TYPE: PRT
<213> ORGANISM: Artificial Sequence
<220> FEATURE:
<223> OTHER INFORMATION: synthetic peptide

<400> SEQUENCE: 6

Glu Phe His Cys
1

<210> SEQ ID NO 7
<211> LENGTH: 5
<212> TYPE: PRT
<213> ORGANISM: Artificial Sequence
<220> FEATURE:
<223> OTHER INFORMATION: synthetic peptide

<400> SEQUENCE: 7

Cys Glu Phe Ala His
1               5

<210> SEQ ID NO 8
<211> LENGTH: 6
<212> TYPE: PRT
<213> ORGANISM: Artificial Sequence
<220> FEATURE:
<223> OTHER INFORMATION: synthetic peptide

<400> SEQUENCE: 8

Cys Glu Ala Phe Arg His
1               5

<210> SEQ ID NO 9
<211> LENGTH: 4
<212> TYPE: PRT
<213> ORGANISM: Artificial Sequence
<220> FEATURE:
<223> OTHER INFORMATION: synthetic peptide

<400> SEQUENCE: 9

Cys Glu His Phe
1

<210> SEQ ID NO 10
```

```
<211> LENGTH: 4
<212> TYPE: PRT
<213> ORGANISM: Artificial Sequence
<220> FEATURE:
<223> OTHER INFORMATION: synthetic peptide

<400> SEQUENCE: 10

Cys Phe Glu His
1

<210> SEQ ID NO 11
<211> LENGTH: 4
<212> TYPE: PRT
<213> ORGANISM: Artificial Sequence
<220> FEATURE:
<223> OTHER INFORMATION: synthetic peptide

<400> SEQUENCE: 11

Cys Phe His Glu
1

<210> SEQ ID NO 12
<211> LENGTH: 4
<212> TYPE: PRT
<213> ORGANISM: Artificial Sequence
<220> FEATURE:
<223> OTHER INFORMATION: synthetic peptide

<400> SEQUENCE: 12

Cys His Phe Glu
1

<210> SEQ ID NO 13
<211> LENGTH: 4
<212> TYPE: PRT
<213> ORGANISM: Artificial Sequence
<220> FEATURE:
<223> OTHER INFORMATION: synthetic peptide

<400> SEQUENCE: 13

Cys His Glu Phe
1

<210> SEQ ID NO 14
<211> LENGTH: 4
<212> TYPE: PRT
<213> ORGANISM: Artificial Sequence
<220> FEATURE:
<223> OTHER INFORMATION: synthetic peptide

<400> SEQUENCE: 14

Cys Asp Phe Glu
1

<210> SEQ ID NO 15
<211> LENGTH: 4
<212> TYPE: PRT
<213> ORGANISM: Artificial Sequence
<220> FEATURE:
<223> OTHER INFORMATION: oligopeptide
<220> FEATURE:
<221> NAME/KEY: variant
<222> LOCATION: 1
<223> OTHER INFORMATION: Xaa = D-Cysteine or L-Cysteine
<220> FEATURE:
<221> NAME/KEY: variant
<222> LOCATION: 2
<223> OTHER INFORMATION: Xaa = D-Glutamic acid or L-Glutamic acid
<220> FEATURE:
```

```
<221> NAME/KEY: variant
<222> LOCATION: 3
<223> OTHER INFORMATION: Xaa = D-Phenylalanine or L- Phenylalanine
<220> FEATURE:
<221> NAME/KEY: variant
<222> LOCATION: 4
<223> OTHER INFORMATION: Xaa = D-Histidine or L- Histidine

<400> SEQUENCE: 15

Xaa Xaa Xaa Xaa
1
```